(12) United States Patent
Mersel et al.

(10) Patent No.: US 11,484,571 B2
(45) Date of Patent: Nov. 1, 2022

(54) PHARMACEUTICAL COMPOSITIONS CONTAINING BETA-2 MICROGLOBULIN AND METHODS OF TREATING AUTOIMMUNE DISEASES

(71) Applicant: BETA INNOV, Paris (FR)

(72) Inventors: Marcel Mersel, Montpellier (FR); Clovis Rakotoarivelo, Montpellier (FR)

(73) Assignee: BETA INNOV, Paris (FR)

( * ) Notice: Subject to any disclaimer, the term of this patent is extended or adjusted under 35 U.S.C. 154(b) by 367 days.

(21) Appl. No.: 15/298,757

(22) Filed: Oct. 20, 2016

(65) Prior Publication Data

US 2017/0035846 A1   Feb. 9, 2017

Related U.S. Application Data

(62) Division of application No. 13/636,438, filed as application No. PCT/IB2011/051476 on Apr. 6, 2011, now abandoned.

(60) Provisional application No. 61/346,617, filed on May 20, 2010.

(30) Foreign Application Priority Data

Apr. 8, 2010   (EP) ..................... 10290188

(51) Int. Cl.
| | | |
|---|---|---|
| *A61P 37/00* | (2006.01) | |
| *A61K 38/17* | (2006.01) | |
| *G01N 33/564* | (2006.01) | |
| *A61K 9/127* | (2006.01) | |

(52) U.S. Cl.
CPC .......... *A61K 38/1774* (2013.01); *A61K 9/127* (2013.01); *G01N 33/564* (2013.01); *G01N 2333/70539* (2013.01); *G01N 2800/10* (2013.01); *G01N 2800/24* (2013.01)

(58) Field of Classification Search
None
See application file for complete search history.

(56) References Cited

U.S. PATENT DOCUMENTS

| | | | |
|---|---|---|---|
| 5,192,549 | A | 3/1993 | Barenolz et al. |
| 7,892,828 | B2 | 2/2011 | Taylor-Papadimitriou et al. |
| 2003/0194401 | A1 | 10/2003 | Yi |

FOREIGN PATENT DOCUMENTS

| | | |
|---|---|---|
| EP | 1669084 | 6/2006 |
| JP | 7118163 | 5/1995 |
| WO | 9116924 | 11/1991 |
| WO | 9964957 | 12/1999 |
| WO | 0224929 | 3/2002 |
| WO | 02102840 | 12/2002 |
| WO | 2004020586 | 3/2004 |

OTHER PUBLICATIONS

Yilmaz, B et al. W. J. Gastroent. 2014;20(31):10916-10920.*
Zissis, M., et al. Am. J. Gastroent. 2001;96:2177-2183.*
Rock et al., J. Immunol. 1993;150:1244-1252.
Halota et al.: "Serum beta-2 microglobulin concentrations in patients with autoimmunologic and chronic C hepatitis", Journal of Autoimmunity, No. SUPPL,1999, p. 98, XP009136217, & 2nd International Congress on Autoimmunity; Tel Aviv, Israel; Mar. 7-11, 1999 ISSN: 0896-8411 abstract, Cited in ISR.
Kochanska-Dziurowicz et al.: "Estimation of the value of serum beta-2-microglobulin concentration in the diagnosis of Hashimoto's disease", Clinica Chimica Acta, vol. 233, No. 1-2, 1995, pp. 101-104, XP002593003, ISSN: 0009-8981 p. 103, Cited in ISR.
Krejsek et al.: "Elevation of serum soluble intercellular adhesion molecule-1 (sICAM-1) and beta-2-microglobulin in Sjogren's syndrome", Clinical Rheumatology, vol. 16. No. 2, 1997, pp. 149-153, XP002593004, ISSN: 0770-3198 pp. 150-151, Cited in ISR.
Glick et al: "Structure based design of mutated beta-2 microglobulin as a novel selective protein drug", Abstracts of Papers American Chemical Society, vol. 222, No. 1-2, 2001, p. BIOL252, XP009136218, & 222nd National Meeting of the American Chemical Society; Chicago, Illinois, USA; Aug. 26-30, 2001 ISSN: 0065-7727 abstract, Cited in ISR.

* cited by examiner

*Primary Examiner* — G. R. Ewoldt
(74) *Attorney, Agent, or Firm* — Nixon & Vanderhye

(57) ABSTRACT

A pharmaceutical product containing β2-microglobulin or a functional variant thereof as an active ingredient in the form of liposomes is provided. The product can increase the concentration of β2-microglobulin in the blood, and can also restore a normal HC/β2-microglobulin molar ratio within membrane MHC-I complexes, or prevent a β2-microglobulin deficit from occurring in the MHC-I complexes, of patients suffering from autoimmune diseases. Methods of treating patients with the pharmaceutical product are also presented.

15 Claims, 11 Drawing Sheets

Figure 1:
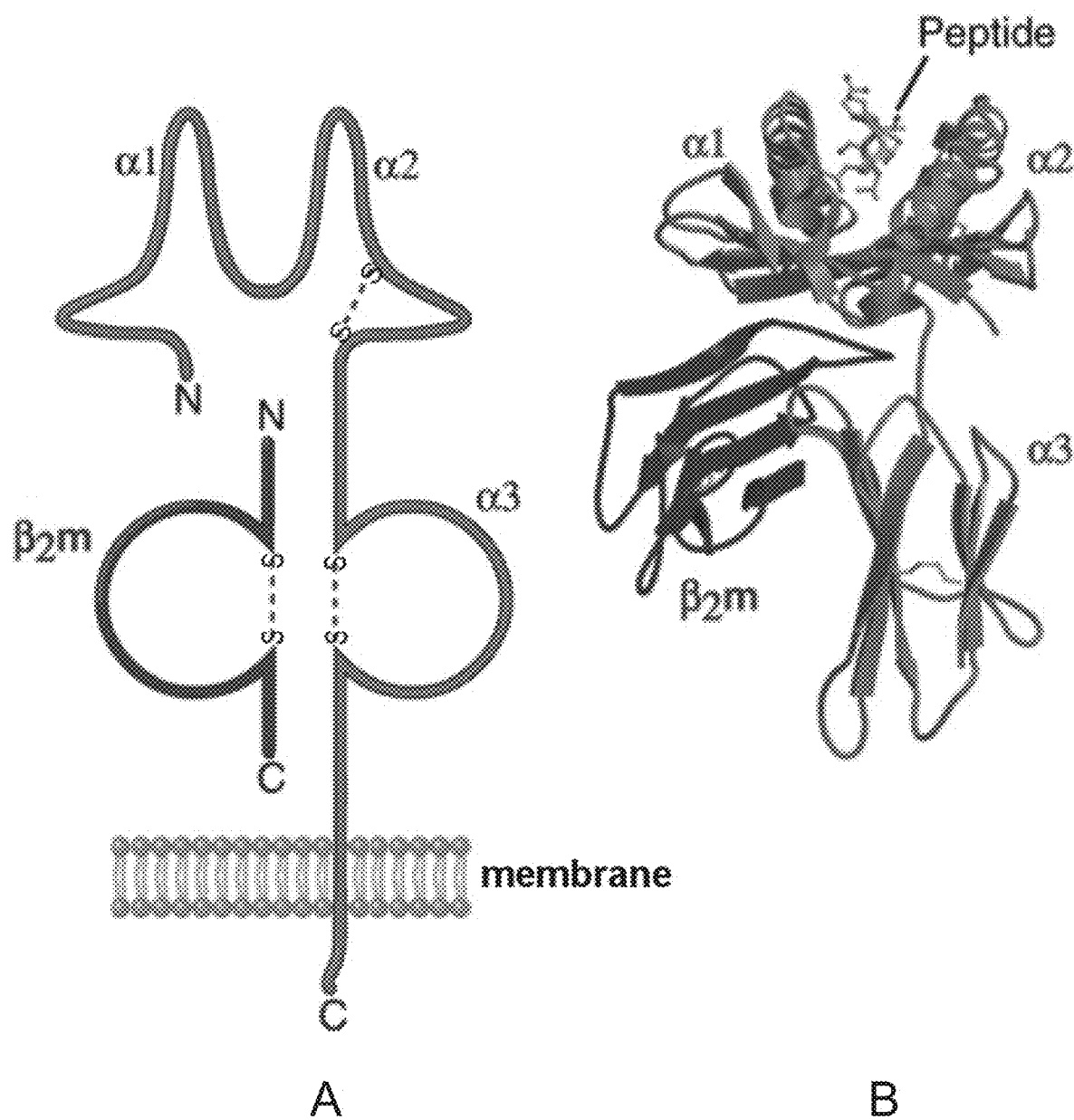

PHARMACEUTICAL COMPOSITIONS CONTAINING BETA-2 MICROGLOBULIN AND METHODS OF TREATING AUTOIMMUNE DISEASES

The present patent application concerns the medical field, in particular that of the treatment of autoimmune diseases.

The invention relates more particularly to the use of the beta2-microglobulin protein (β2m) as active ingredient, in particular in pharmaceutical compositions intended for the treatment of autoimmune diseases, such as, for example, multiple sclerosis or Crohn's disease.

Preamble

The β2m protein is a protein having an average molecular weight of approximately 11.6 kDa, generally formed from 99 amino acids, which enter into the constitution of the major histocompatibility complex (MHC I or HLA I) [Cunningham B. A. et al. The complete amino acid sequence of beta-2-microglobulin (1973) *Biochemistry* 12: 4811-4821].

It is to be recalled that the MHC I histocompatibility complex plays a central role in the recognition of "self" and "not-self" by the immune system. These complexes are present on the surface of most human cells, with the exception of the erythrocytes. On their surface they present a high number of antigens on the basis of which the T lymphocytes (CD8) are capable of discriminating the cells of an individual from the cells that are foreign thereto, diseased or undergoing a tumor transformation process.

The MHC I complexes are composed of a glycosylated heavy chain (HC), of approximately 44 kDa, and of a light chain, the β2m, which associates non-covalently with the extracellular domain of the heavy chain. The α chain of MHC I is composed of three extracellular domains, (at α2 and α3) and of a transmembrane segment as indicated in FIG. 1A. The β2m associates with a sequence of amino acids situated in the zone where the end of the α1 domain and the start of the α3 domain in the HC are in proximity [Gussov, D. et al. (1987), The human beta-2-microglobulin gene: primary structure and definition of transcriptional unit (1987) *Journal of Immunology* 139:3132-3138]. The genes coding for the MHC I molecules have been numbered in the order of their discovery and classed into groups (A, B and C) and complexes (D, H and G).

The antigen-presenting cells (APCs) use the complexes of MHC I type as antigen presenters to T-cells (CD8) of the immune system. The antigens presented by MHC I are generally constituted by a variety of polypeptides having 8 to 10 amino acids, which results from the splitting of endogenous proteins by the proteasome. These antigens are loaded onto the peptide cavities present on the surface of the sub-units (HC and β2m) of the MHC I complexes during their formation within the endoplasmic reticulum. Once the antigens have been loaded, the MHC complexes are exported to the surface of the cell. The anchoring of the MHC I complex to the plasma membrane is then provided by the transmembrane domain of the heavy chain situated at the α3 domain.

The subunit formed by the β2m protein is distinguished from the heavy chains in that the sequence is practically invariable and in that its polypeptide chain is not glycosylated.

Even if its physiological role has not yet been fully elucidated, it has been shown that the β2m protein plays a dominant role with regard to the other protein forming the MHC I complexes, on the one hand, upon assembly of the MHC I/antigen complex [Androlewicz M J., et al. (1994) MHC class I/β2-microglobulin complexes associate with TAP transporters before peptide binding, Nature 368, 864-867], in which the β2m protein specifically binds to the TAP-1 protein, [Corr et al. 1992. Endogenous peptides of a soluble major histocompatibility complex class I molecule H-2Lds: sequence motif, quantitative binding and molecular modeling of the complex, *JEM,* 176(6):1981-92], making it possible to ensure that the conformation of the antigen binding site is maintained [Ljunggren, H.-G. (1990) Empty MHC class I molecules come out in the cold. *Nature.* 346, 476-480] and, on the other hand, when the MHC I/antigen complex is exported to the cell surface. The β2m is involved in the folding of the heavy chain and is also found to be involved in the presentation of the antigen to the T-cells (CD8). The β2m also contributes to the stability of the MHC-I/antigen complex [Neefjes, F. F. et al. (1993) Selective and ATP-dependent translocation of peptides by the MHC-encoded transporter. *Science.* 261 (5122): 769-771].

Transgenic animals lacking any β2m prove viable, but present a weakened immune response, making them more susceptible to viral and parasitic infections. The reduction in the immune response in these animals appears to be correlated with the fact that their cells present very few antigens with regard to their MHC I complex and that the majority of their T lymphocytes are not functional [Pereira P., et al. (1992) Blockade of transgenic gamma delta T cell development in beta 2-microglobulin deficient mice, *EMBO Journal* 11:25-31].

The β2m protein is also described as being involved in the glycosylation of heavy chains in the Golgi apparatus [Sege et al. (1981) Role of beta2-microglobulin in the intracellular processing of HLA antigens. *Biochemistry.* 20 (16), pp 4523-4530].

The β2m protein is also involved in other phenomena such as the regulation of intercellular signaling and the correct folding of key proteins, such as HFE (Human hemochromatosis protein) which regulates the flow of iron in the cell.

It has also been established since the end of the 1980's that β2m may favorably improve the antigen response and be used as a vaccine adjuvant to stimulate the immune response linked to the T lymphocytes (CD8).

Numerous documents indicate that β2m may thus be incorporated into vaccine compositions in combination with molecules having the task of inducing an immune reaction, such as specific virus or tumor antigens.

In such vaccine compositions, β2m may be present in different forms, purified or recombinant. Genetic constructions have thus been described in which the gene coding for β2m is fused with genetic sequences coding for immunogenic peptides with the aim of expressing fusion proteins intended to elicit a specific immune reaction in-vivo [WO 99/64957].

By itself, the β2m protein is very weakly immunogenic, since it is not glycosylated. On account of this, in the above vaccine compositions, β2m is always used as an adjuvant and not as an active ingredient.

This is doubtless due to the fact that, to date, no therapeutic effect of β2m has been observed capable of justifying its use in pharmaceutical compositions.

Apart from in vaccination, certain prior art documents indicate inactivated or modified forms of the β2m protein in therapeutic compositions.

The international application WO 02/102840 thus describes a β2m rendered non-functional intended to form inactive MHC I complexes, which can no longer activate the CD8 T lymphocytes. The MHC complexes so formed are used as a "lure" for the immune system with the object of obtaining an immunosuppressant effect.

Another international application WO 02/24929 describes therapeutic compositions in which the β2m is conjugated to the HFE protein as a vector, to deliver drugs (active ingredients of those compositions) to the intracellular compartment.

It should be noted that in these types of applications, the β2m protein is not used in its wild-type functional form as active ingredient, but as a pharmaceutical support or vector, in the presence of active ingredients not directed to the MHC.

Moreover, in contrast to any therapeutic application, the β2m protein is often used as a marker for different pathologies, in particular as a means of diagnosis.

Thus, the immune deficiency syndrome in the AIDS disease, which may reveal itself many years after the infection with HIV, is preceded by an abrupt increase of the β2m concentration in the blood.

Certain publications [Wu C. H. et al. (2001) *Oncogene* 20:7006-20] stress that the increase in the β2m concentration correlates with and is perhaps involved with the development of certain cancers, in particular bone cancer and prostate cancer [Gross M. et al. (2007) *Clin. Cancer Res.*, 13:1979-1986]. For other cancers, drops in the β2m serum concentration are observed, as in cancer of the colon [Kaklamanis L. et al. (1992) *Int J. Cancer* 57:379-385].

The dosage of β2m in the blood (and more particularly the blood serum), the cerebrospinal fluid or the saliva, is frequently used in the diagnosis of certain infectious or parasitic diseases but also, primarily, for the diagnosis of certain diseases of the kidney, of the lymphatic system, rheumatism, inflammatory diseases, and neurological diseases such as Alzheimer's and frontotemporal dementia [Davidsson P. et al. (2002), Proteome analysis of cerebrospinal fluid proteins in Alzheimer patients Clinical Neuroscience and Pathology 13: 611-615; Hansson S. F. et al. (2004), Validation of a prefractionation method followed by two-dimensional electrophoresis-Applied to cerebrospinal fluid protein from frontotemporal dementia patients Proteome *Science* 2:1-11].

In persons considered to be in good health, the average concentration of β2m in the blood remains relatively constant, less than or equal to 2 mg/l, which is not the case in the above-mentioned diseases, in which that concentration may attain values as high as 4.0 mg/l.

For certain pathologies, the increase in serum β2m could be caused by increased "shedding" (release of cell surface proteins) of the β2m [Bellotti V., et al. (1999) *Cell. Mol. Life Sci.*, 55-977-991].

The plasma β2m circulating in the blood is normally filtered in the kidneys by the glomeruli, then reabsorbed and catabolized in the tubules.

Studies have shown that half the plasma β2m (free form of the β2m), which is renewed each day, comes more particularly from the recycling of the MHC-I complexes. This renewal by itself thus appears to contribute a high production of serum β2m of approximately 150 mg/24 h for a person of average size. However, the "turn-over" would appear to stabilize the serum concentration at 2 mg/l.

In patients under dialysis, for whom β2m is not eliminated by the kidneys, the accumulation of β2m in the body fluids has deleterious consequences. In particular, it induces arthropathies and neuropathies by formation of amyloid plaques in certain connective tissues (nervous and articular) [Ohshi K., et al. Pathogenesis of beta2-microglobulin amyloidosis (2001) *Pathol. Int* 51:1-10].

In osteoarthritis (arthrosis), β2m is described as having an inhibiting effect on the proliferation of the chondrocytes, a consequence of which is to accentuate the destruction of the cartilages [WO 2004/020586].

In the case of certain autoimmune diseases, such as multiple sclerosis (MS), it is common to monitor changes in the concentration of β2m in patients, to anticipate the onset of inflammatory episodes [Bagnato, F., (2003), beta-2 microglobulin and neopterin as markers of disease activity in multiple sclerosis *Neurol. Sci.* 24:51301-51304]. The concentration of β2m is then preferably measured in the cerebrospinal fluid since the concentration of β2m in the blood is considered as too variable [Caudie C. et al. (2005), Valeurs usuelles et utilité diagnostique de la β2-microglobuline dans le liquide céphalorachidien *Ann. Biol. Clin.* 63(6): 631-637; Ryu O. H., et al. (2006) *Rheumatology*, 45:1077-1086].

The involvement of β2m in autoimmune diseases remains unclear and would merit further study.

The autoimmune diseases form a large set of diseases the symptoms of which may be attributed to hyperactivity of the immune system, with the presence or absence of autoantibodies, directed against substances or tissues which are normally present in the body.

It is certain that the immune response against "self" in autoimmune diseases results from the activation of the T lymphocytes via the MHC system and several mechanisms may cause this.

In the immune system:
  By induction of autoantibodies using T cells by presentation of antigens known by said autoantibodies. This is the case of systemic lupus erythematosus (SLE), Hashimoto's thyroiditis, multiple sclerosis (MS), insulin dependent diabetes (type I), etc.

In cells:
  induction of an autoimmune response by activation of T cells specific to a viral antigen;
  Alteration with regard to APC-MHC-I/TcR (T cell receptor) recognition and with regard to the signaling cascade(s) of the activated T lymphocyte.
  Improper assembly in the APC of the components of the MHC-I system.
  Defect(s) in the operation of the regulatory cells.

At molecular level:
  Molecular mimicry or tolerance;
  MHC I as an autoantigen;

The autoimmune diseases are generally considered to result from a conjunction of a genetic predisposition and of an infectious episode during which the body develops a immune reaction to its own antigens. However, the exact causes of these diseases have not been identified precisely.

The most widespread autoimmune diseases are rheumatoid polyarthritis, Sjögren's syndrome, Hashimoto's thyroiditis, Addison's disease, systemic lupus erythematosus, scleroderma, fibromyalgia, myositis, ankylosing spondylitis, insulin dependent diabetes of type I, Crohn's disease, Celiac's disease and multiple sclerosis (MS).

Among what are referred to as the "orphan" diseases, there are numerous other disorders that are suspected of also being autoimmune diseases. Amyotrophic lateral sclerosis (ALS) is one of those diseases, for which no effective treatment is currently available.

Two types of autoimmune diseases should be distinguished: the specific autoimmune diseases and the non-specific autoimmune diseases.

In the non-specific diseases, different organs are affected, causing systemic diseases such as rheumatoid arthritis, systemic lupus erythematosus, Sjögren's syndrome and scleroderma.

The specific diseases are especially limited to certain organs. The most common are insulin dependent diabetes, thyroid diseases, Addison's disease, a few diseases of the kidneys, of the lungs, of the digestive system, and especially multiple sclerosis.

Current therapies comprise a range of approaches from anti-inflammatories to immunosuppressants through antimetabolites and anti-cancer drugs. By way of example the following are used: non-steroidal anti-inflammatory drugs (NSAIDs), glucocorticoids, antimetabolites (methotrexate, azathioprine), cyclophosphamide, sulfasalazine, gold salts, cyclosporin A, mycophenolate, and leflunomide.

Recently, interferon β has been recommended for MS and the derivatives of chloroquine (used against malaria) are recommended for the treatment of lupus erythematosus and of rheumatoid polyarthritis.

These treatments, used for treating other diseases, are not very well adapted and have numerous undesirable side effects, in particular when they are used over the long-term. Moreover, although they may enable the symptoms of those diseases to be at least partially attenuated, they do not enable remission of the diseases to be obtained.

The inventors designated by the present application took a particular interest in the situation of four patients affected by apparently distinct autoimmune diseases:

A first patient (PI) suffering from a non-specific autoimmune disease, that is to say not affecting a specific organ, but also suffering from Hashimoto's thyroiditis and primary Sjögren's syndrome;

A second patient (P2) suffering from MS, originally, with duodenal lymphocytic infiltration subsequently;

A third patient (P3) suffering from Celiac's disease;

A fourth patient (P4) suffering from Hashimoto's thyroiditis and from Celiac's disease.

For these patients, the inventors sought to establish the ratio of the quantities HC (MHC-ABC)/β2m coming from the lymphocytes, isolated from the blood of the patients using the conventional methods indicated later.

Surprisingly, this HC/β2m ratio proved to be on the increase in these four patients, compared with that of control donors, whereas there serum β2m concentration was average: approximately 1.9 mg/l for P1, 1.8 mg/l for P2, 1.1 mg/l for P3 and 1.1 mg/l for P4. (cf. table I).

TABLE 1

Determination of the different forms of β2m in patients suffering from autoimmune diseases

| Patients | Serum β2m (a) | HC/β2m proteins (b) | HC/β2m membranes (c) |
| --- | --- | --- | --- |
| P1 | 1.9 | 1.3 | 1.8 |
| P2 | 1.8 | 1.1 | 1.7 |
| P3 | 1.1 | 1.6 | 1.5 |
| P4 | 1.1 | 1.2 | 2.1 |

HC: heavy chains of the MHC I
(a) Concentration of β2m in mg/l;
(b) HC/β2m calculated from the total lymphocyte proteins.
(c) HC/β2m calculated on the plasma membranes isolated from a purified lymphocyte fraction.

The results of table 1 above show an imbalance in the HC/β2m ratio. These results have revealed an unexpected situation, whereby the MHC-I membrane complexes present in those four patients is apparently significantly deficient in β2m relative to the HC concentration, without this increasing the concentration of free β2m in the blood.

These observations are to be compared to the controls in good health, who show a HC/β2m ratio in the neighborhood of 1. By contrast, β2m appears to be sequestrated in the intracellular compartment in the patients affected by the autoimmune diseases.

These results surprised the inventors and led them to formulate the hypothesis that the four autoimmune diseases affecting the patients could have a deficit in β2m in the membrane MHC-I complexes as a common origin. More generally, an HC/β2m imbalance in the MHC complexes would appear to contribute to the appearance of the disorders encountered in numerous autoimmune diseases.

According to this hypothesis set out later, the autoimmune reaction, in the context of the pathologies from which four patients suffer, is not apparently the consequence of a general increase of free β2m in the blood, but on the contrary, originates with a local β2m deficit in the membrane MHC-I complexes, which is liable to alter the presentation of the antigens to the T cells (CD8).

It should be noted that this hypothesis in no way excludes the involvement of the β2m in the activation of the T lymphocytes and in the inflammatory process, as it may have been described in the prior art.

Given these first observations, the inventors carried out the analysis of HC/β2m in the total lymphocyte proteins present in other patients suffering from MS or Crohn's disease, and were able to find that the HC/β2m ratio coming from the lymphocytes of these patients was also greater than of control patients.

On the basis of these results, the inventors have developed pharmaceutical compositions of which the main active ingredient is the β2m protein in a functional form.

The purpose of these compositions is to mitigate a deficit in β2m in the membrane MHC-I complexes in patients affected by autoimmune diseases.

FIG. 1: Diagrammatic representation of an MHC complex of type I in a plane (A) and in space (B). The heavy chain (HC) is constituted by 3 extracellular domains (α1, α2 and α3) and one transmembrane domain. The light chain (β2m), which is extracellular, inserts between the membrane and the location where the α1 and α3 of the heavy chain are in proximity. Figure B shows the position of the peptides (antigens) presented by the heavy chain.

Figure 2:
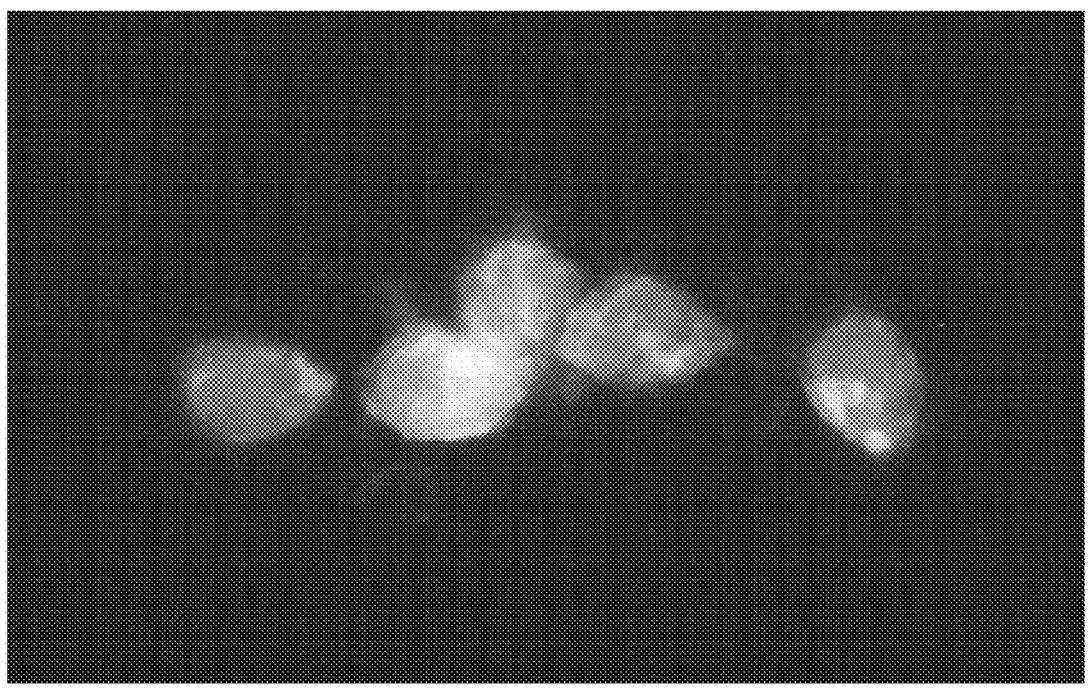

FIG. 2: Photograph (×630) of lymphocytes placed in contact with liposomes in accordance with the invention. The liposomes have been prepared according to the dialysis method described in Example 2. The liposomes (light spots) are adsorbed on the membrane of the lymphocytes (HLA-ABC). The cell nucleus is intact (gray).

Figure 3:
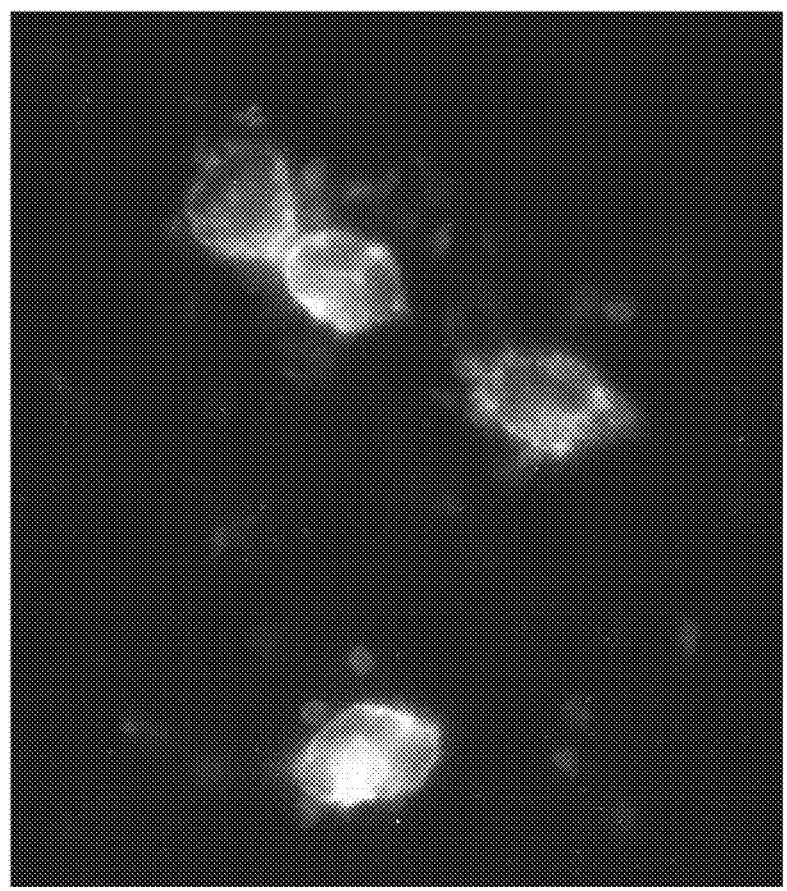

FIG. 3: Photograph (×630) of lymphocytes placed in contact with liposomes in accordance with the invention containing albumin. The protein (albumin) is rendered fluorescent with DAPI. It forms darker spots, detected by immunofluorescence, penetrating the lighter lymphocytes (HLA-ABC positive).

Figure 4:
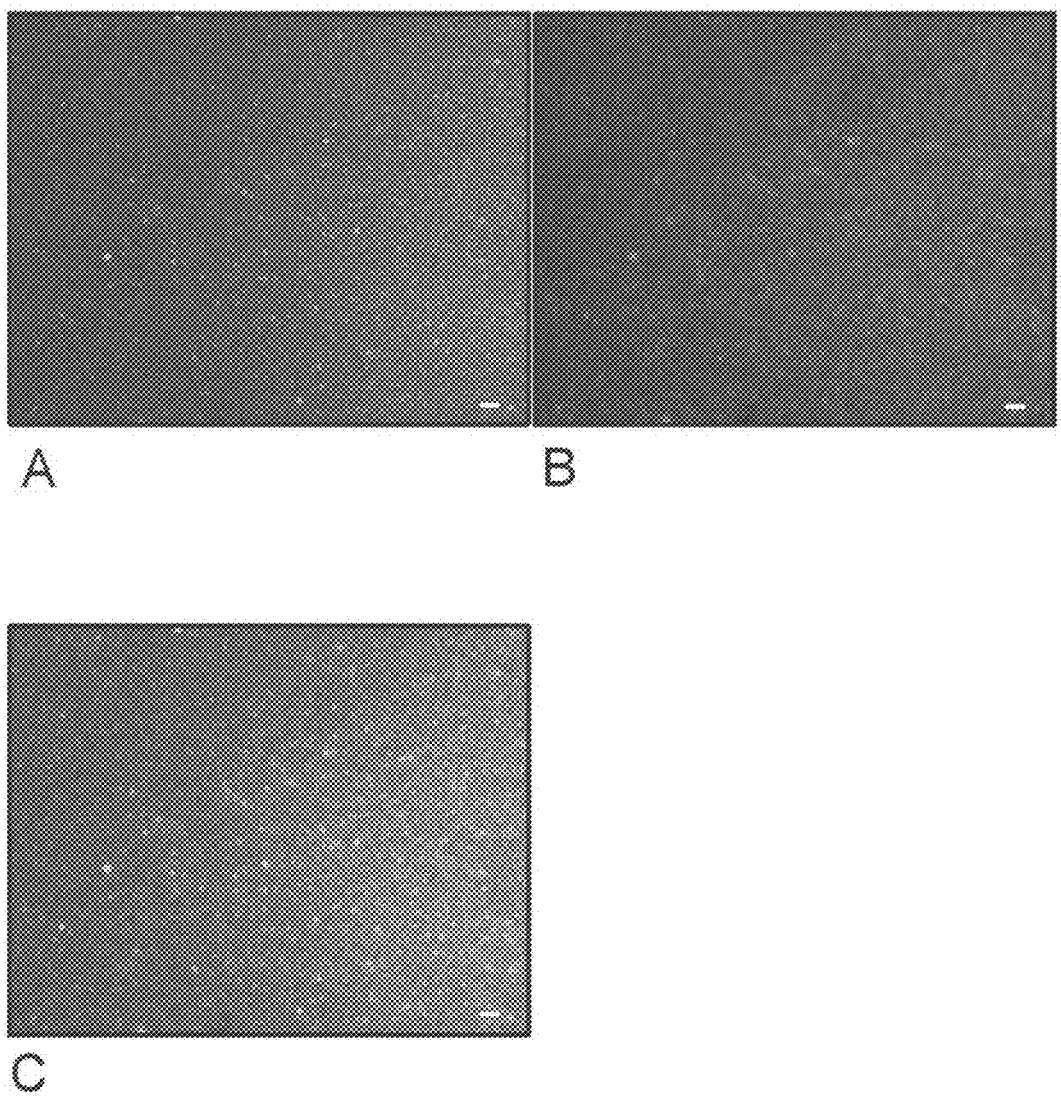

FIG. 4: Photograph (×630) of liposomes prepared using the extrusion method (green) and containing fluorescent β2m (TRITC). A: Fluorescence emitted by the fluorescent lipid NBD-PC-Oleyl contained in the liposomes. B: Fluorescence emitted by the fluorophor (rhodamine B isothiocyanate) coupled to the β2m. C: Superposition of the two fluorescences A and B.

Figure 5:
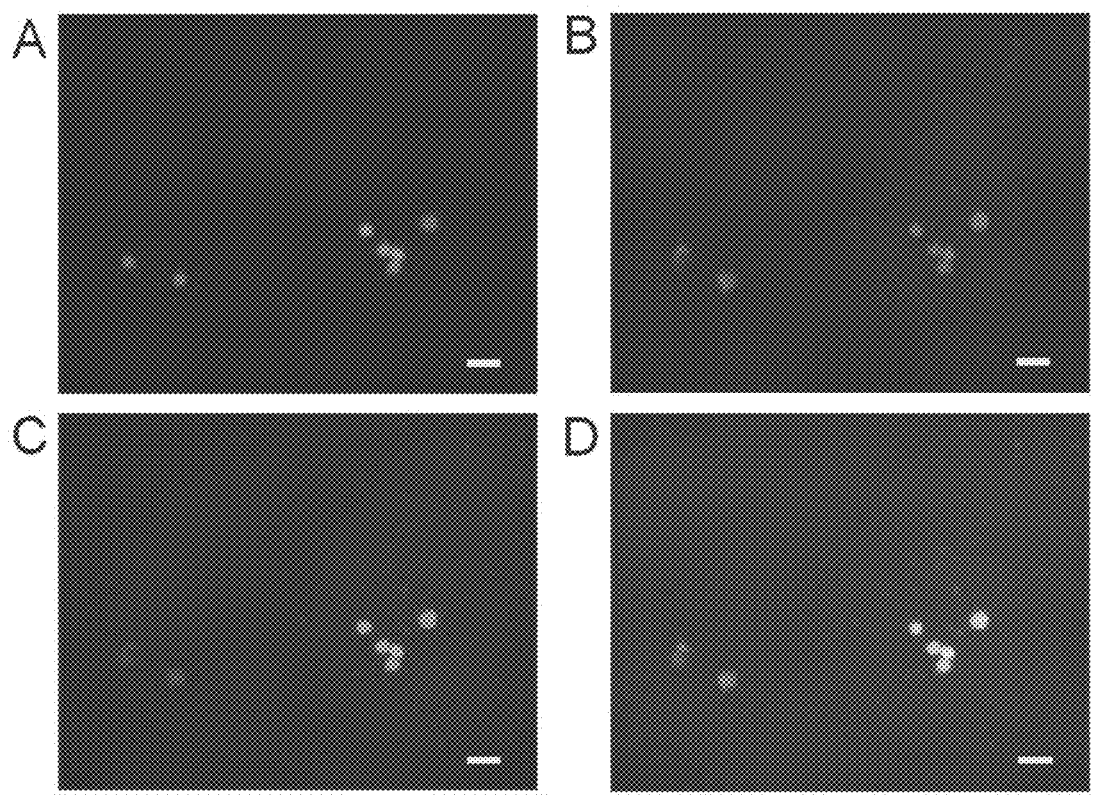

FIG. 5: Photograph (×630) of lymphocytes purified from a patient (P1) and incubated with liposomes prepared according to the extrusion method and containing fluorescent β2m (TRITC). A: fluorescence emitted by the Hoechst 33342 marker which colors the nuclei of the lymphocytes in blue. B: Fluorescence emitted by the fluorophor (rhodamine B isothiocyanate) coupled to the β2m. This marking shows the incorporation of β2m into the lymphocytes that have become red in color. C: Fluorescence emitted by the green fluorescent lipid NBD-PC-Oleyl contained in the liposomes. This marking shows the association of the liposomes with the lymphocytes. D: superposition of the B and C marking (yellow color) Scale bar: 10 μm.

Figure 6:
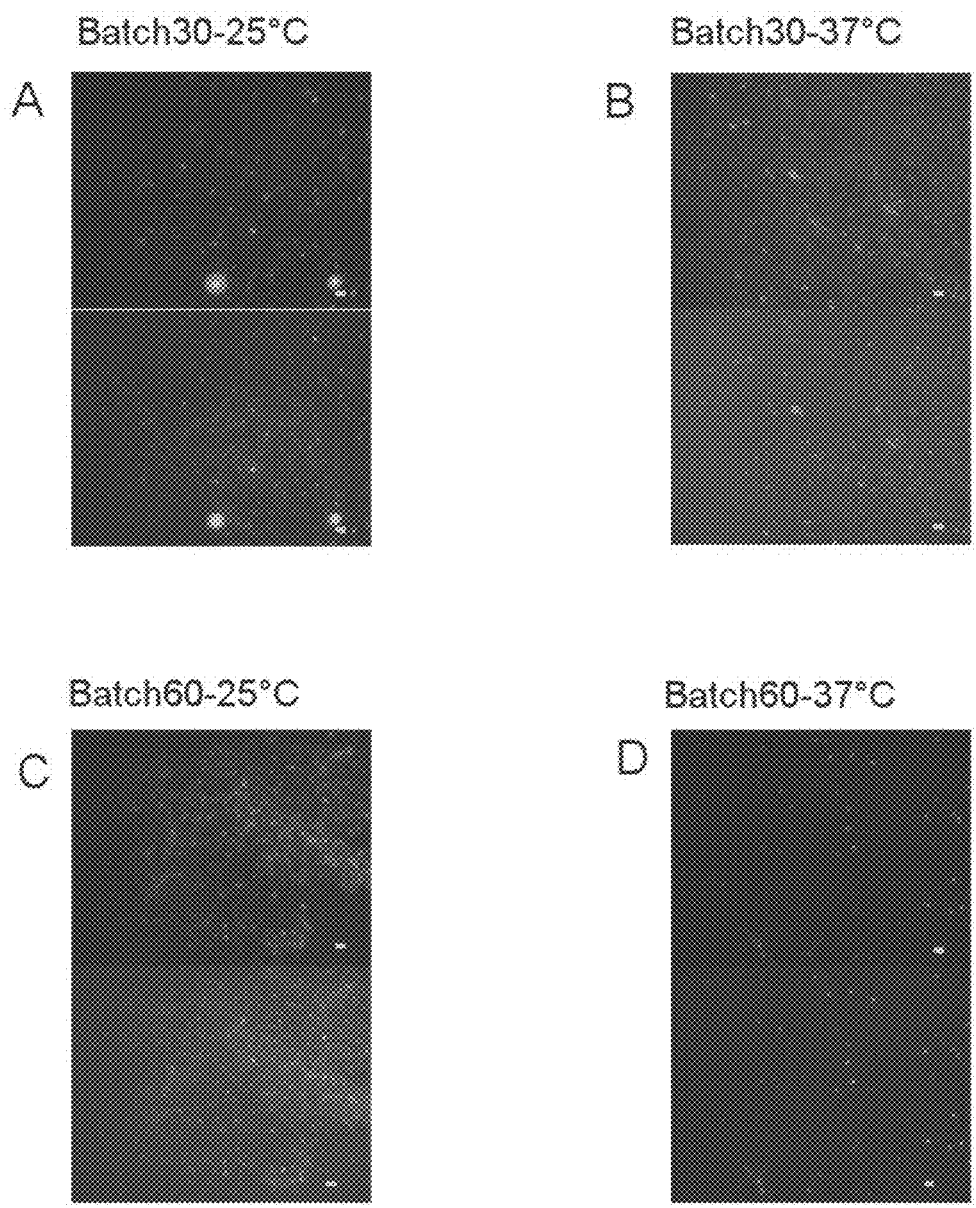

FIG. 6: Microscopic examination by fluorescence of liposomes containing albumin (TRITC) after 30 days storage at two different temperatures (25° C. and 37° C.). Through observation, major differences between the different types of preparation and storage cannot be distinguished. A and B: Batch 30 (30 mg prot./150 ml). C and D: Batch 60 (60 mg prot./150 ml). Bottom: Fluorescence emitted by the fluorescent lipid NBD-PC-Oleyl contained in the liposomes. Top: Fluorescence emitted by the fluorophor (rhodamine B isothiocyanate) coupled to the albumin. Scale bar: 200 nm. Enlargement ×630.

Figure 7:
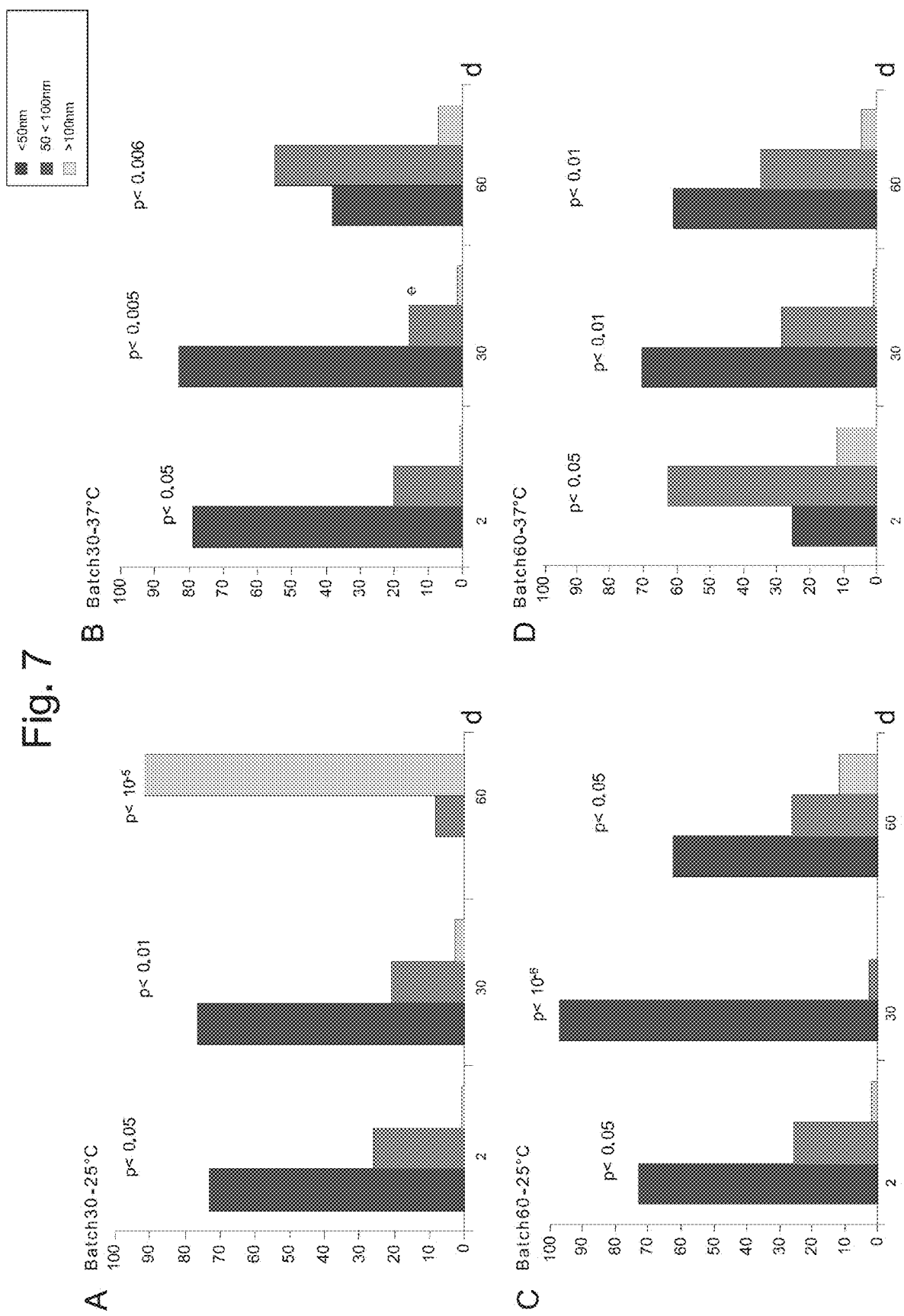

FIG. 7: Size distribution (%) of the liposomes (<50 nm, between 50 and 100 nm, >100 nm) containing albumin according to time (2, 30 and 60 days) and storage temperature (25° C. and 37° C.). A and B: Batch 30 (30 mg prot./150 ml), C and D: Batch 60 (30 mg prot./150 ml).

Figure 8:
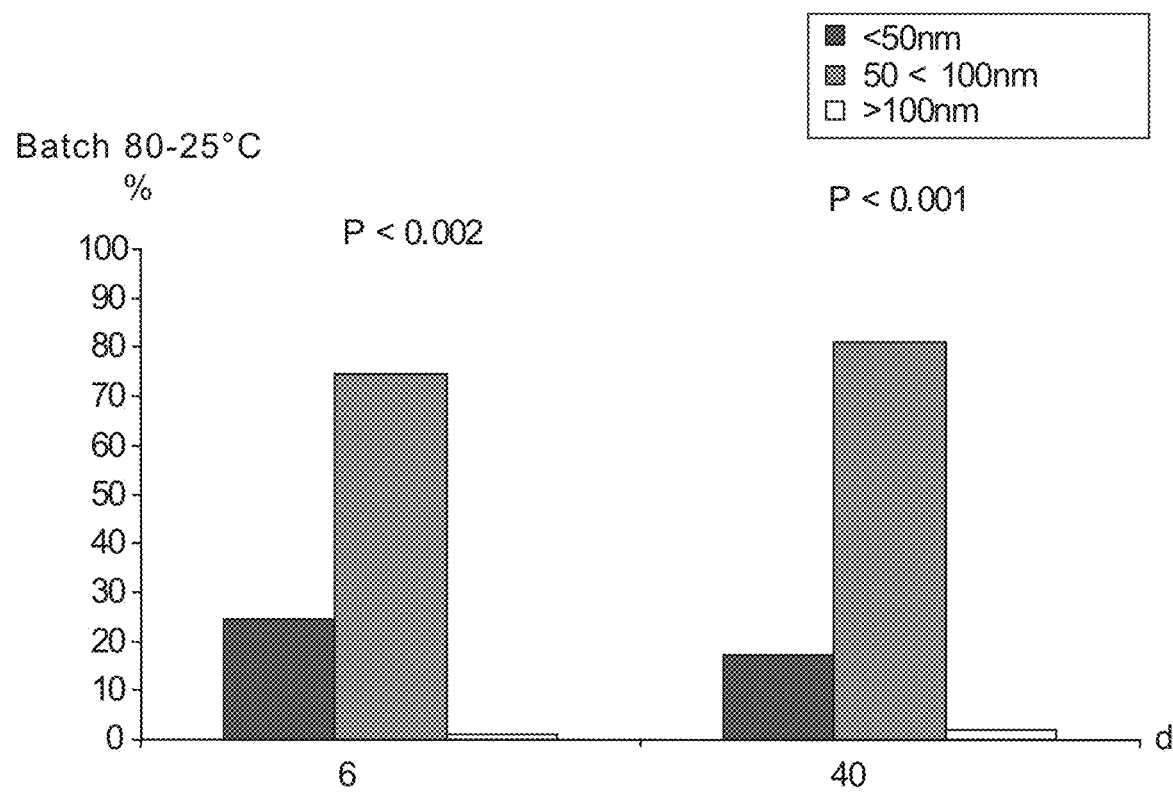

FIG. 8: Size distribution (%) of the liposomes (<50 nm, between 50 and 100 nm, >100 nm) containing a high concentration of β2m (Batch 80 mg prot./150 ml) according to time stored at 25° C. for 6 and 40 days.

Figure 9:
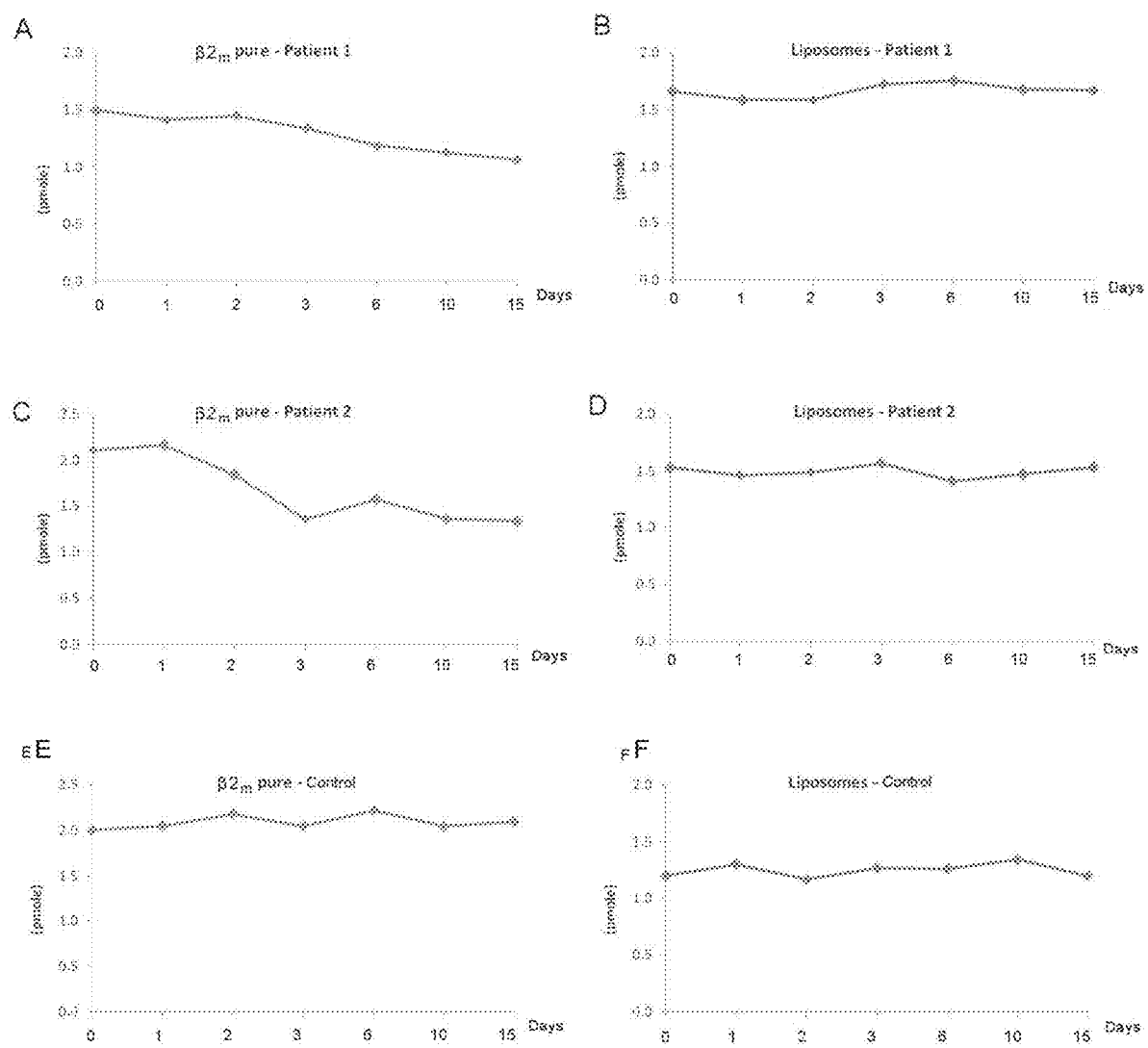

FIG. 9: Degradation profiles for the pure or liposome-coated β2m by sera of patients or healthy donors over time. A and B: pure/liposome preparation of β2m (serum patient 1: 51-year old woman, suffering from Hashimoto's disease). C and D: pure/liposome preparation of β2m (serum patient 2: 73-year old woman, rheumatoid polyarthritis). E and F: control patient, healthy 62-year old man.

Figure 10:
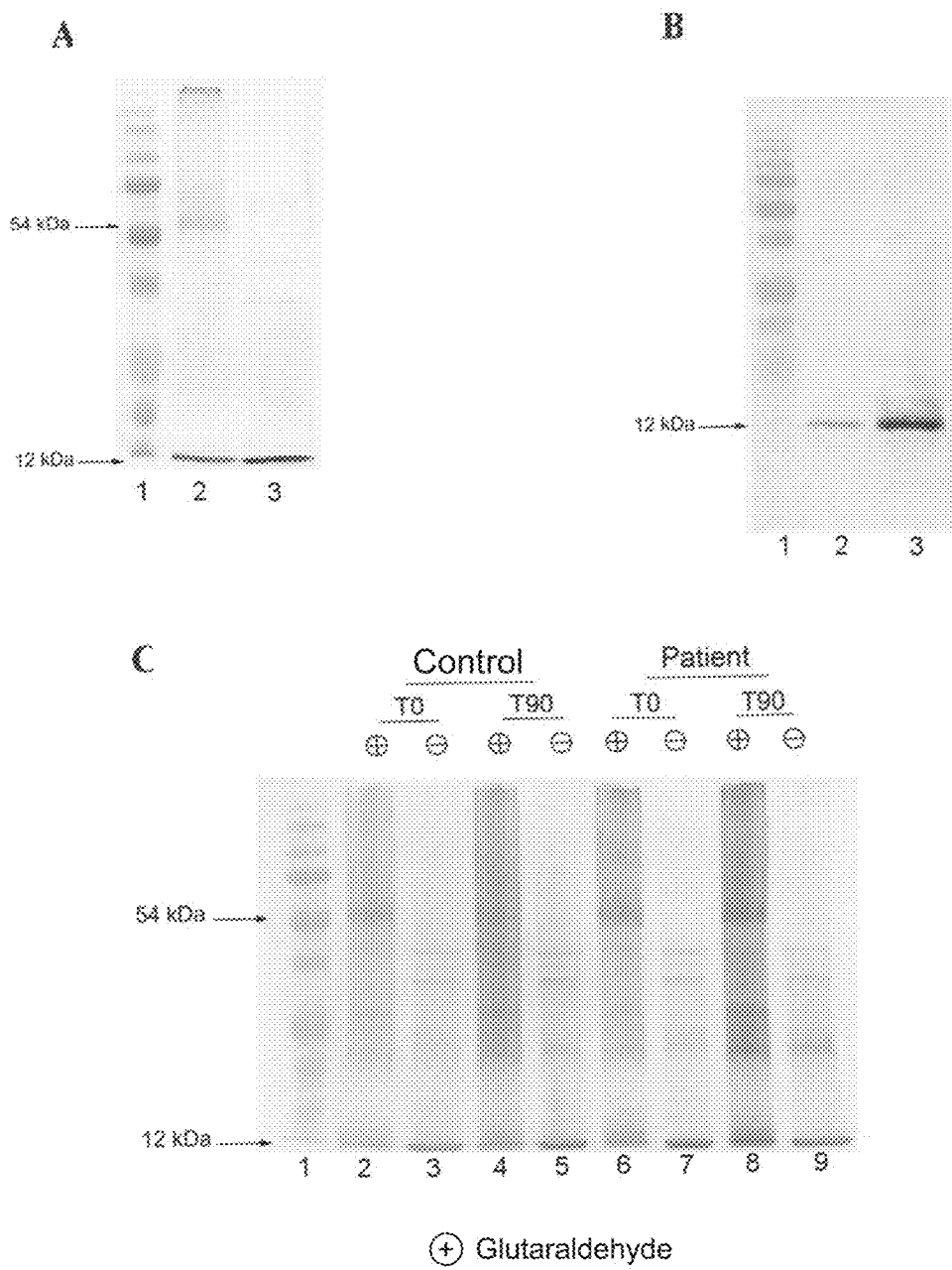

FIG. 10: Electrophoresis gel of protein showing the association between β2m (liposome preparation) and the heavy chains of MHC-I on the cell surface of lymphocytes purified from patients. A: In the presence of glutaraldehyde, the HLA-β2m complexes are viewed at 55 kDa and the free β2m at 12 kDa. The band at 12 kDa on the track without glutaraldehyde represents the cellular β2m (lane 3). B: Quantifying the membrane expression of the β2m. This control makes it possible to validate the use of glutaraldehyde for the preparation of the HLA-β2m complexes. C: Comparison of the lymphocytes from a patient suffering from multiple sclerosis (woman, 39 years old) and from a healthy donor (man, 67 years old) after incubation with a liposome preparation of β2m for 90 minutes. The β2m contained in the liposomes binds more on the lymphocytes coming from the patient (in the presence of glutaraldehyde) than it does in control.

Figure 11:
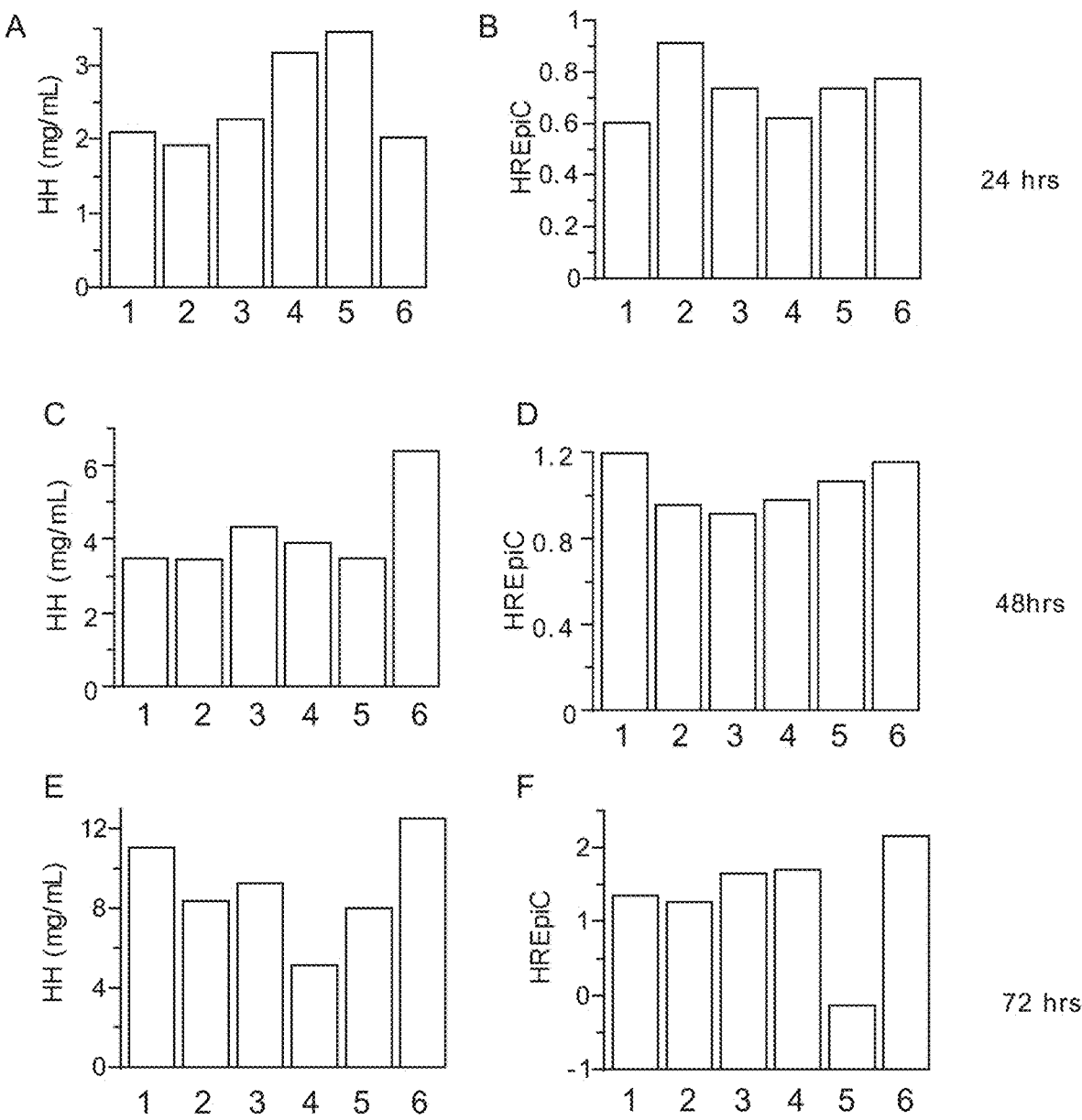

FIG. 11: "In vitro" toxicity assays of free β2m or in liposomes on human hepatic and renal cells. A, C and E: assays on HH hepatic cells after 24, 48 and 72 hours of exposure. B, D and F: HREpic renal cells after 24, 48 and 72 hours of exposure. 1. control. 2. control and non-loaded liposomes. 3. 3 μg free β2m. 4. 3 μg β2m in liposome form (batch 66 μg/150 ml). 5. 6 μg free β2m. 6. 6 μg β2m in liposome form (batch 132 μg/150 ml). Total protein content was estimated by the BCA method.

Figure 12:
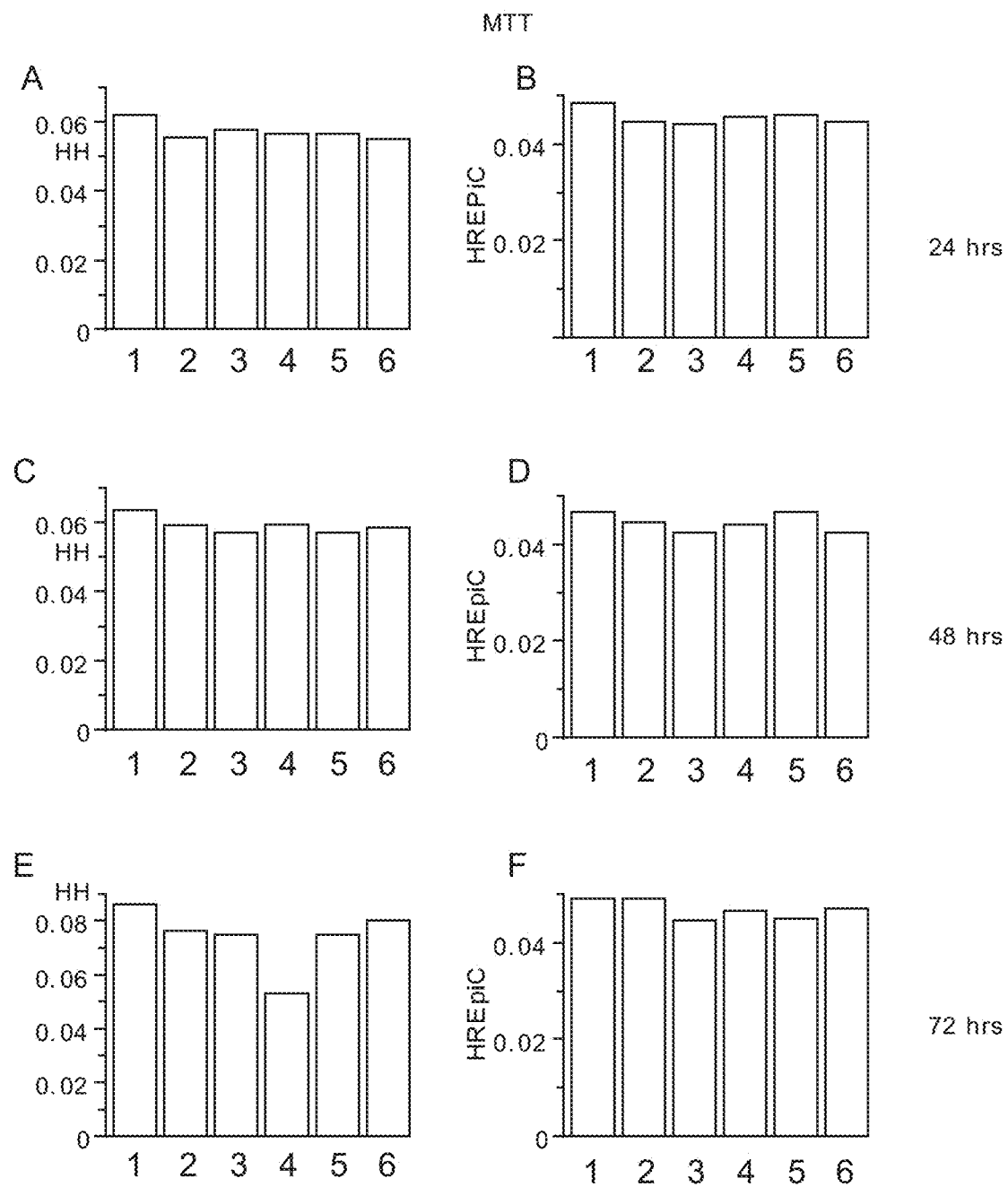

FIG. 12: "In vitro" toxicity assays of free β2m or in liposomes on human hepatic and renal cells. Same labels as in FIG. 11. Result of MTT assays for viability.

DETAILED DESCRIPTION

The present invention thus relates to a use of the β2m protein as active ingredient, in particular for the preparation of a medicament.

The β2m protein is preferably the human form of the protein, purified or recombinant, of which a reference polypeptide sequence as well as the genetic determinants are described in the GENEBANK database, under the accession number CAG33347.

If it is purified, the β2m may be obtained from the sera of healthy donors.

It may also be envisaged to have recourse to chemical synthesis since the protein may be used in a non-glycosylated form.

The present therapeutic use of β2m extends to the functional variants of that protein, that is to say to its isoforms, to mutated copies or to fragments of that protein, characterized in that they have the same functionality as the wild-type protein, that is to say the same therapeutic effect as described in the present application, it being possible however for that effect to be reduced or increased in its intensity relative to said wild-type protein.

Functional variant more particularly designates a polypeptide capable of associating with the MHC complexes present on the surface of cells, the polypeptide sequence of which is at least 70%, preferably at least 80%, more preferably at least 90%, and still more preferably at least 95%, identical to the polypeptide sequence of the human β2m protein (the comparison of the sequence being made, for example, using the ClustalW software application).

A functional variant of the β2m preferably consists of a fragment of the β2m protein, presenting the same therapeutic effect, or even the same biological activity.

Such functional variants may also result from the expression of nucleotide sequences cloned in an expression vector or in a gene therapy vector.

Numerous publications describe, for example, the presence of isoforms of β2m in rodents [Goding J. W. and Walker I. D. Allelic forms of 132-microglobulin in mouse (1980) *Proc. Natl. Acad. Sci. USA* 77: 7395-7399] and in man [Davidsson P. et al., Proteome analysis of cerebrospinal fluid proteins in Alzheimer patients (2002) *Clinical Neuroscience and Pathology* 13: 611-615; Hansson S. F. et al., Validation of a prefractionation method followed by two-dimensional electrophoresis-Applied to cerebrospinal fluid protein from frontotemporal dementia patients (2004) *Proteome Science* 2:1-11]. These isoforms, which are distinguished more particularly by a different isoelectric point (pl), are considered as functional variants of β2m.

Such functional variants may have certain advantages in terms of the effectiveness of the product or its formulation relative to the purified human protein (solubility, greater stability, reduced proteolytic degradation).

The present invention concerns pharmaceutical compositions comprising β2m or one of the functional variants of β2m, as active ingredient.

Preferably, the β2m or its functional variant forms the sole active ingredient of said compositions.

Within the meaning of the present invention, an active ingredient is a substance which enters into the composition of a medicament and which is responsible for the pharmacodynamic or therapeutic properties thereof. An adjuvant is not considered as an active ingredient within the meaning of the present invention.

More preferably, the invention relates to a pharmaceutical composition consisting of β2m or a functional variant of β2m contained in a pharmaceutically acceptable carrier or vehicle, said pharmaceutically acceptable carrier or vehicle preferably being a liposome.

According to a preferred aspect of the invention, the β2m is administered alone with said pharmaceutically acceptable carrier, or a physiological solution, in accordance with the regulatory recommendations and requirements.

According to the invention, the β2m is more particularly used for its capacity to restore a normal HC/β2m ratio within the membrane MHC-I complexes in a patient.

The HC/β2m ratio is preferably treated with regard to the lymphocytes, in particular the B cells. The HC/β2m ratio corresponds to the molar ratio of the HC and β2m sub-units in the purified MHC I complexes.

Preferably, this ratio is returned to a level comparable to that of a patient not suffering from disease. More preferably, the β2m is used with the aim of reducing the HC/β2m ratio in a patient to attain a molar ratio close to 1.

The present invention is more particularly directed to preventing a deficit of β2m from occurring in the MHC-I complexes in patients suffering from autoimmune diseases.

The use of the β2m according to the invention is thus more particularly intended for the treatment of autoimmune diseases.

The inventors have been able to determine that a deficit of intracellular or membrane β2m could give rise to a HC/β2m ratio greater than 1 or even 2 in certain patients suffering from autoimmune diseases. The invention is thus directed to returning said HC/β2m to a value close to physiological values i.e. preferably less than 2, more preferably less than 1.5 and still more preferably less than 1.2.

The invention may of course apply to any disease linked to an imbalance in the HC/β2m ratio in the MHC I complexes, other than the autoimmune diseases.

Within the meaning of the present invention, the pathologies linked to organ transplants or transplant rejection, are not considered as autoimmune diseases, nor as diseases caused by a defect in recognition of the "non-self" by the immune system. To be precise, transplant rejection is considered here as resulting from a recognition of "non-self" by the immune system, and not as a defect in recognition of "self".

The analyses carried out by the inventors in different patients indicate that a HC/β2m ratio, calculated on the basis of the total lymphocyte protein, greater than 1.2 may be observed at least for the following diseases: rheumatoid polyarthritis, systemic lupus erythematosus, Sjögren's syndrome, scleroderma, fibromyalgia, myositis, ankylosing spondylitis, insulin dependent diabetes of type I, Hashimoto's thyroiditis, Addison's disease, Crohn's disease, Celiac's disease, amyotrophic lateral sclerosis (ALS) and multiple sclerosis (MS). Although the question is still under debate within the scientific community, ALS is assimilated to an autoimmune disease, in view of the results obtained.

The invention concerns more particularly the development of a medicament for increasing the ratio of blood β2m to a concentration comprised between 2.5 and 12 mg/l, preferably between 3 and 8 mg/l, more preferably between 3 and 5 mg/l, to mitigate the HC/β2m deficit of the membrane MHC-I complex.

As described below, in the experimental part of the present invention, the medicament according to the invention may consist in a liposome preparation comprising β2m or a functional variant thereof. The liposomes may be manufactured using different techniques known to the person skilled in the art, such as those illustrated in the examples of the present application. Different lipids constituting the liposomes may be used [Medical Application of Liposomes (1986) edited by Kunio Yagi, Japan Scientific Societies Press, Tokyo, Karger].

A preferred medicament of the invention in this respect consists of a liposome loaded with β2m.

Preferably, the β2m or a functional variant of that protein constitute the only active ingredients contained in said liposome preparation.

It is advantageous to use a liposome according to the invention as a medicament because it enables the β2m to be protected from proteolytic attacks which may take place and because it enables the β2m to be delivered in targeted manner to the MHC-I complexes, in particular by fusion of the liposome with the phospholipids, which constitute the cell membranes.

According to another aspect of the invention, a gene therapy vector coding for the β2m or for one of its functional variants is used to synthesize the protein in-vivo, preferably in the environment of the MHC complexes. Such a gene therapy vector may be contained in liposomes.

The invention thus also relates to a gene therapy method comprising a step of in-vivo or ex-vivo expression of the β2m or of a functional variant thereof, as active ingredient. Different types of viral or non-viral vectors, described in the literature, may be adapted to express the β2m protein for this purpose [Urnov et al. (2005) Highly efficient endogenous human gene correction using designed zinc-finger nucleases, *Nature*, 435:577-579]. Preferably, the gene therapy vector according to the invention enables the expression in the human body of the β2m protein (or of its functional variant) with the exception of any other active ingredient, and preferably of any other polypeptide.

According to an aspect of the invention, a patient may be treated by perfusion with a solution of liposomes containing the β2m or a vector expressing that protein or by transfusion of lymphocytes from patients placed in contact with the β2m beforehand. This placing in contact may be carried out by an "ex vivo" incubation of lymphocytes extracted from a sample of blood taken previously from the same patient.

According to a preferred aspect of the invention, the medicament comprising the β2m is prepared in a saline form. A preferred process for preparing the medicament consists in incubating the β2m in saline form, ex-vivo, in contact with the serum of the patient for whom the medicament is intended.

The pharmaceutical compositions according to the invention described above may take any appropriate form known to the person skilled in the art for their oral administration, by injection, perfusion or inhalation.

Another aspect of the invention concerns the diagnosis of autoimmune diseases, more particularly the diagnosis of the diseases cited above, by in-vivo or in-vitro determination of the HC/β2m ratio of the MHC I complexes.

The method of diagnosis according to the invention preferably comprises one or more of the following steps consisting of:
i) taking cells from a patient in whom an autoimmune disease is to be screened, preferably lymphocytes;
ii) extracting the MHC I complexes from those cells, and if necessary;
iii) determining the respective quantities of HC and of β2m contained in said complexes;
iv) establishing the HC/β2m molar ratio; and
v) comparing the HC/β2m ratio obtained with the results obtained previously from other patients.

The HC/β2m ratio may be established for the whole of the cell (HC/β2m cell ratio), or, preferably, for the membrane (HC/β2m ratio of the membrane MHC I complexes). Preferably, the method of diagnosis according to the invention comprises a step of comparing the HC/β2m ratio with that of a control, or else in the context of monitoring a patient, with other previously determined ratios.

The respective quantities of the proteins of HC and β2m may be determined in standard manner according to the methods known to the person skilled in the art, for example by quantitative immuno-detection (e.g. ELISA, Immunodot, "Western Blot", autoantigen microarrays etc.). The extraction of the MHC-I complexes is performed according to the known protocols of extracting cell and membrane proteins.

The method of diagnosis according to the invention may be implemented in the context of therapeutic monitoring of patients suffering from various autoimmune diseases.

The following examples are intended to supplement the description of the invention without limiting the scope thereof.

EXAMPLES

1—Analysis of the Components of the HLA-I Membrane Complex of the Lymphocytes in Patients Suffering from Autoimmune Diseases Without being bound by theory, the inventors have developed the working hypothesis that an increase in the HC/β2m ratio may result in reactions of autoimmune type. In particular, the inventors have considered that an excess of HC, a reduction in β2m, at the level of the MHC-I complexes, or both at the same time, could give rise to a phenomenon of "over-exposure" of "self" to the TcRs. Note that the β2m protects certain regions of the HCs and specifically determines the presentation of the "non-self" to the CD 8 T-cells [Hill, D. M. et al. (2003), A dominant negative mutant β2-microgobulin blocks the extracellular folding of major histocompatibility complex class I heavy chain. *JBC*. 278: 5630-5638].

To verify this hypothesis, a first analysis was made to determine the molar quantities of HC and of β2m in the MHC I complexes extracted from lymphocytes of four patients. The results of these analyses are presented in Table 1, commented upon above.

The lymphocytes were isolated from the blood of healthy donors and from the patients according to the method of Lightbody J. [*Manual of Clinical Immunology*, Rose N R., Friedman H. Editors American Society for Microbiology Washington (DC), 1976, pages 851-857] modified by Hofman F. M. et al. [*Ann. J. Clin. Pathol.* (1982) 77:710-716]. The MHC-I complexes are detected on the whole lymphocytes or on the plasma membranes prepared according to the method of Warley A. et al. [*Biochim. Biophys-Acta* (1973), 323: 55-66] with a few modifications. The detection of the protein components of the MHC-Is was carried out by electrophoresis (SDS-PAGE system), according to Laemmli U.K. [*Nature* (1970) 227:680-685] then by electro-transfer onto membranes of PVDF and immunoblotting according to the method of Towbin H. et al. [*Proc. Natl. Acad. Sci. USA* (1979) 76:4350-4354]. The revelations were conducted by secondary antibodies coupled to alkaline phosphatase using an NBT-DCIP mixture.

It was verified that the excess of the heavy chains was indeed of membrane origin by isolation of the plasma membranes and use of the method of binding to glutaraldehyde described later.

As indicated above, four other cases of MS, and two cases of Crohn's disease show a cell ratio of HC/β2m>1. These observations incited the applicant to develop an experimental approach enabling the balance of HC/β2m (MHC-I) to be restored, in particular by use of liposomes.

2—Preparation of Liposomes Loaded with β2m:

2.1—Evaluation of the Quantity of β2m to be Delivered to the Patients

To bring the β2m on the surface of the lymphocytes into excess, its concentration in the blood should be increased within "reasonable" limits in order not to trigger the signaling channels on the cells having a potential for multiplication.

Given the facility with which β2m detaches from the membranes and circulates in the blood and renal system, the blood β2m concentration should be brought to between 3 mg/l and 8 mg/l (the normal concentration varies at around 2 mg/l of blood). This increase leads to the adsorption of the β2m at the surface of the cells.

Note that the major histocompatibility complexes of type I are composed mole/mole of heavy chains (MW≈43 kDa) and of β2m (MW≈12 kDa). A complex (MW≈55 kDa) is thus composed, by weight, of 79% heavy chain and 21% light chain.

The average protein content of a lymphocyte is $650 \times 10^{-12}$ g and the protein content of its plasma membrane represents only 1% of its total content, i.e. $6.5 \times 10^{-12}$ g. If it is considered that the MHC-I only represents 1% at most of the total content of membrane proteins of a quiescent lymphocyte, the β2m content is thus about $1.4 \times 10^{-14}$ g per lymphocyte.

By taking average physiological parameters, $2 \times 10^6$ lymphocytes/ml of blood and 5 liters of blood per individual, the range in "weight" of the total MHC-I/individual (concerning the lymphocytes) would be $1.4 \times 10^{-6}$ g to $1.8 \times 10^{-6}$ g of lymphocyte β2m. These figures are maximum figures in that our first estimates show values preferentially ranging from $0.2 \times 10^{-9}$ to $500 \times 10^{-9}$ g on average in the patients. As the average quantity in the blood is 10 mg of β2m per individual, i.e. a quantity very substantially greater than that present on the surface of the lymphocytes, it appears that, in normal conditions, a ratio substantially less than 1 already exists between membrane β2m and serum β2m. It is thus not unreasonable to increase the ratio of β2m in the blood circulation (increasing its oncotic partial pressure) to make up for the membrane deficit in β2m.

The administration of the β2m may be carried out in two ways:

(1) Administration of liposomes loaded with β2m. This type of pharmaceutical carrier is current for the administration of peptides, antibodies, genetic material etc. The use of liposomes ("artificial" or synthetic membranes) promotes the contact between the cell surface and the active ingredient;

(2) Incubation of the active ingredient in saline form with the serum of the patients before administration. The object of this incubation is that the lipoproteins of the serum act as a vector in the manner of liposomes.

The degree of incorporation of β2m in the lymphocytes further to the administration by method 1 or 2 may be compared with a control administration; in the latter case, the β2m saline perfusion is administered at 0.10 mg/ml (total volume 150 ml), which provides 3 mg of β2m per liter of blood (batch with 15 mg of β2m/150 ml of liposome solution designated "Batch 15").

2.2—Formulation of the Liposomes

For the preparation of the liposomes (for 1 ml): after evaporation of dichloromethane ($CH_2Cl_2$) containing the constituents to dryness under nitrogen, a film containing the phosphatidylcholine, with or without addition of cholesterol, with or without addition of sphingomyelin or with addition of cholesterol and sphingomyelin is constituted. For the three compounds (phosphatidylcholine, cholesterol and sphingomyelin) the proportions are respectively 10 M, 2 M and 1 M i.e. for 1 ml of final solution 7.60 mg, 0.76 mg and 0.38 mg. To this film there is added 1 ml of a saline solution (PBS 10 mM. pH=7.4; HANKS, Tris/Glycine or DMEM) containing 2 mg of β2m. The molarity remains the same for each of the compounds if liposomes made from phosphatidylcholine (10 M), from phosphatidylcholine (10 M) and from cholesterol (2 M), from phosphatidylcholine (10 M) and from sphingomyelin (1 M) are produced. However other molarities concerning the lipid components may be used. The quantities of proteins may be different and the pH may be greater than 7.4 depending on the case. The dispersion of the lipid film is carried out by stirring up to 3 hours at a temperature between 20 and 37° C.

The liposomes are formed by the so-called "detergent/dialysis" method, or else by the so-called "extrusion" method. For the latter, the solution (Lipofast®, Sodexim S.A., 51140 Muizon, France) is passed 41 times through filter membranes of 100 nm in polycarbonate under a pressure of 69 bars. The liposomes obtained are of homogenous size. The liposomes, in this case, are kept for 2 days at 4° C. and added to the lymphocyte suspension (diameter<100 nm; FIG. 4). On larger scale, the solution (3 l/hr; sodexim 2770; emulsifflex c3; sodexim s.a.) is then passed 4 times at a pressure of 450 bars to obtain SUVs (small unilamellar vesicules).

In "pre-pilot" assays, in order to show the incorporation of the β2m in liposomes, the adsorption of the liposomes on the cell surface and the transfer of the protein from the liposome to the inside of the cells, we produced fluorescent liposomes. According to the assays, liposomes were prepared which fluoresce at 520 nm or 572 nm. For this, 0.5 M of NBD-PC (1-oleyl-2-(-6-(((7-nitro-2-1,3-benzoxadiazol-4-yl)amino)hexanoyl)-sn-glycero-3-phosphocholine) (excitation at 490 nm and emission at 520 nm) or 0.5 M of Liss Rhod PE (1,2-dioleyl-sn-glycero-3-phosphatidylethanolamine-N-(lissamine rhodamine B sufonyl) (ammonium salt) (excitation at 541 nm and emission at 572 nm) were added to the lipid mixture before evaporation and obtainment of the lipid film (see above).

At pre-pilot scale, the liposomes were produced by the detergent/dialysis method. By this technique, well-calibrated and stable SUVs were also obtained.

Briefly, after stirring up to 3 hours at a temperature between 20 and 37° C., the micellar suspension is dialyzed against a saline solution containing β2m as well as 4 μM (0.8 mg/ml) of n-hexyl-βD-glucopyranoside for 12 h at 4° C. in a microdialysis apparatus. The dialysis membranes have an cut-off of 3.5 kDa and the n-hexyl-βD-glucopyranoside (detergent) is diluted to least 1 ppm in the final solutions.

The liposomes obtained have a size of approximately 200 nm diameter. They are stable over 3 months, at least, at ambient temperature and contain at least 0.1 mg (β2m)/ml of initial solution.

Alternatively, green fluorescent liposomes are produced according to the extrusion method (Lipofast) and contain human β2m purified from urine (Sigma, USA) at a concentration of 0.6 mg/ml. β2m is labeled by rhodamine B isothiocyanate, which fluoresces in the red (TRITC exitation at 540 nm emission at 625 nm). The coupling between β2m and rhodamineis carried out according to Riggs, J L, Seiwald, J H, Bruckhalter, J H, Downs, C M and Metcalf T G [*Am. J. Pathol.* 1958, 34: 1081-1097]. After coupling, the protein is purified in a Sephadex column (Pharmacia, Sweden; G-10, bead volume 9 ml; internal column diameter 0.7 mm). The column is swollen in PBS (Biorad, 10 ml de phosphates, 150 mM NaCl, pH 8.3) Protein is eluated (4.5-7.0 ml) in diluted PBS with Milliq water (1:1). The liposomes (FIG. 4A) are purified on an identical column (2.5-6.5 ml) and two times concentrated with a rotovapor (Buchi, Switserland). The lymphocytes isolated from patient P1 are incubated as described previously during 90 minutes and observed under fluorescence microscope (FIG. 4B). Our results show that 89% of the lymphocytes incorporate β2m (FIGS. 4 and 5).

2.3—Application of Test Liposomes onto Lymphocytes Maintained "Ex Vivo" in Culture To show the relevance of formulating the β2m protein for the purpose of targeting the MHC complexes of the lymphocytes, in the form of liposome suspensions, lymphocytes were incubated with liposomes loaded with albumin, a protein that is possible to detect by fluorescence using a relatively simple technique.

The incorporation of the protein into the liposomes and the application of the liposomes produced according to the protocol described above on the basis of phosphatidylcholine with Liss Rhod PE were tested ex-vivo.

The protein was rendered fluorescent by marking with fluorescamine, a compound whose fluorescence is comparable with that of DAPI (Di Amino Phenyl Indol; excitation at 372 nm and emission at 456 nm). The albumin crystallized from bovine serum was rendered fluorescent using binding by covalency of the fluorescamine on the N-terminal end of the protein, using the method described by Flames B. D. et al. [Gel Electrophoresis of Proteins, a practical approach, Flames B D. and Rickwood D. eds. *The practical* Approach Series, 2$^{nd}$ Edition. IRL Press, Oxford, New York, Tokyo. p. 67] except that the marking is carried out in a Tris-Hcl (25 mM)/Glycine (192 mM) (pH=8.3) buffer not containing detergent (SDS). The liposomes formed, as described earlier, contain 2 mg of fluorescent albumin per ml of liposome solution.

Next, 0.2 ml of a suspension of lymphocytes (Hank's/0.5 mM EDTA, pH=7.4), containing 250 000 lymphocytes, was incubated with 0.2 ml of the liposomes so formed containing albumin (Buffer 25 mM Tris-Hcl/192 mM Glycine, pH=8.3) for 1 hour at 37° C. in a moist atmosphere saturated with $CO_2$ (5%).

Finally, control liposomes (200 μl), control lymphocytes (200 μl) and lymphocytes treated by liposomes loaded with protein (200 μl) were sedimented on coverslips treated and covered with polylysine, and laminin, using a method described by Rakotoarivelo C et al. [Receptors to steroid hormones and aromatase are expressed by cultured motoneurons but not by glial cells derived from rat embryo spinal cord (2004) *Neuroendocrinology* 80:284-297].

The preparations were observed directly by epifluorescence microscope (Axiovert; Zeiss, Germany) or fixed with a solution at 4% (ply) of paraformaldhehyde in water for 30 minutes, the coverslips being rinsed 3 times with PBS (160 mM, pH=7.2). The preparations were gently rendered permeable, with 0.1% of Triton X-100 (v/v), prepared in PBS, for 5 min.

The cells were marked by primary anti H LA-ABC antibodies. In certain cases, the cell nuclei were marked with Hoechst (fluorescence 450 nm blue emission, DAPI). The primary antibodies, produced in rabbits, are the same as those used for the "Western blot". The primary antibodies are diluted to 1/50 and the secondary antibodies bound to FITC (green fluorescence) and produced in the goat and are diluted to 1/160. The incubations of the antibodies were carried out in PBS containing 2% bovine serum Albumin. For the ×63 lens, the coverslips were mounted with Fluorsave (Calbiochem, USA).

The photographs of FIGS. 2 and 3 show that the liposomes are adsorbed on the surface of the lymphocytes and that the marked protein, contained in the liposomes, is deposited on the membrane surface of said lymphocytes.

The results clearly demonstrate the feasibility of the experimental approach that we propose to restore the HC/β2m membrane equilibrium.

2.4—Stability of Liposomes (FIGS. 6 to 8)

The "test" liposomes obtained above containing albumin were tested in various conditions in order to evaluate their stability over time.

The stability was tested on batches 30 (corresponding to 30 mg of Albumin for 150 ml of liposome) and 60 (corresponding to 60 mg of Albumin for 150 ml of liposome) against time and incubation temperature.

The lipids constituting the liposomes were composed of 636 nmol of PC and 31.8 nmol of NBD-PC-Oleyl. After evaporation to dryness under a stream of nitrogen, the mixture of lipids is solubilized drop by drop with strong stirring with 1 ml of PBS (pH adjusted to 7.2) containing 200 or 400 µg of albumin (Sigma, USA) (batches 30 and 60, respectively). Next, the liposomes were obtained by mechanical extrusion with the Liposofast-basic system (Sodexim, France). Each batch was then purified in a Sephadex G10 column. At a set time, 50 µl of each batch was deposited on a poly-D-lysine/laminine-coated coverslip and incubated at 37° C. for 12 h. Next, the biological material was bound by using glutaraldehyde for 30 at 4° C. The images (stability at 1 month of storage, FIG. 6) were taken using the Axiovert 200 (Zeiss) epifluorescence microscope and recorded with the Axion vision software application. Regarding the statistical studies (FIG. 7), the diameter of the liposomes was measured using Serf software (http://www.org/serf). For the study of each batch, the liposome population was divided into three classes: <50, between 50 and 100 nm and >100 nm diameter. The heights of bar charts represent the percentage of each size sub-population. The batch 60 kept at 37° C. shows the greatest stability for 60 days of storage: 95%, of the liposomes have a diameter<100 nm, which is an ideal diameter for the transfer of protein to the cell surface.

As for batch 80 (80 mg of β2m; FIG. 8), this was tested for storage at 25° C. in order to minimize contamination and evaporation, for 6 and 40 days. The preparation method was the same as the previous one for batches 30 and 60 (albumin) except that non-fluorescent β2m was used (533 µg/ml of PBS) and the purification was carried out by dialysis cassette (membrane with 20 kDa cut-off, Thermo Scientific, USA). The bar chart of FIG. 8 clearly shows that at this stage of storage 98% of the liposomes maintain the ideal size, and this during up to 40 days, for the transfer of β2m to lymphocytes (i.e. diameter<100 nm).

2.5—Protection of the Exogenous β2m Conferred by the Liposomes Against Proteolytic Degradation by Human Sera (FIG. 9)

Sera were taken from healthy donors and donors suffering from autoimmune diseases (Hashimoto's thyroiditis, rheumatoid polyarthritis). These sera were incubated (90 µl) for 15 days at 25° C. in the presence of 2 µg of pure β2m (Sigma-Aldrich, USA) or in liposome form (Batch 30 liposomes corresponding to 30 mg of β2m per 150 ml of liposomes). The total reaction volume was 130 µl, completed if necessary with PBS (sodium phosphate 10 mM, sodium chloride 150 mM, pH=7.2). 10 µl from that reaction medium (corresponding to 150 ng), completed to 30 µl with denaturing buffer (SDS-PAGE, Laemmli) containing 6 M of urea, was successively removed at 0, 1, 2, 3, 6, 10 and 15 days. These samples were kept at −20° C. until analysis.

After collecting all the samples, these were incubated for 1 h at 50° C. Next, the proteins were separated by SDS-PAGE on 12% acralamide gel (% T=12, % C=2.6) containing 4 M of urea.

After electro-elution on a polyvinylidene difluoride (PVDF) membrane, the presence of β2m was detected by immunoblotting and the intensity of the corresponding band was quantified with ImageJ (NIH, USA). By the use of a standard curve, the number of pixels so obtained was converted into pmoles of β2m ($10^{-12}$ moles). The graphs presented in FIGS. 9 A to F represent an example of results obtained and express the quantity of β2m (in pmoles) over time. It can be noted that in the persons suffering from autoimmune diseases, the free β2m added to the serum is degraded over time, which is not the case in the control.

In conclusion, there is a progressive and significant degradation of the free β2m by the serum of autoimmune patients which is not found in the control. On the other hand, this degradation is not observed when the β2m is encapsulated in liposomes. To be precise, the liposomes appear to protect the β2m against degradation by serum, since no significant reduction in the quantity was observed.

In conclusion, the liposomes protect the β2m from the degradation by serum.

2.6—Association of the β2m Contained in the Liposomes with the HLA I Heavy Chains Located on the Membrane Surface (FIG. 10).

In a healthy person and in physiological conditions, the molecules of β2m expressed on the lymphocyte surface are bound non-covalently to the HLA heavy chains with a ratio of 1:1.

In order to view and quantify these protein associations, we developed a technique enabling those proteins, among which the HLA-β2m dimers, to be linked together covalently The development of this technique was necessary to calculate the exact membrane HC/β2m ratio and to show that the addition of β2m in liposome form specifically associates with the heavy chains of HLA-I.

For this we exploited the capacity of a dialdehyde, glutaraldehyde, to bind the amine groups of the proteins by its two aldehyde groups. These aldehyde groups are linked together by a flexible chain of three methylenes which enables glutaraldehyde to statistically crosslink two amine groups coming from two interacting proteins (Sun, T. T., et al. (1974) Protein-protein proximity in the association of ribosomal subunits of *Escherichia coli*: crosslinking of 30S protein S16 to 505 proteins by glutaraldehyde or formaldehyde. *J. Mol. Biol.* 87(3): 509-22).

According to this procedure, 5 million lymphocytes purified by MSL were washed once with PBS (pH=7.2) to eliminate possible traces of free amines, then pelleted by centrifugation at 10 000 g for 10 min and the supernacent liquid eliminated. The cells were then incubated for 5 minutes at ambient temperature in 1 ml of PBS containing 0.25% of glutaraldehyde. During this incubation, the tube was inverted several times.

The cessation of the reaction was obtained by the addition of 100 µl of tris 1 M (pH=7.2), the excess amine groups provided by the Tris buffer neutralizing the glutaraldehyde. The lymphocytes were retrieved by centrifugation at 10 000 g for 10 min, then washed in 1 ml of PBS in order to eliminate traces of glutaraldehyde. After centrifugation, the pellet was retrieved in 400 μl of Laemmli buffer containing 4 M of urea, comprising antiproteases (Roche Diagnostics GmBH, Germany) and 5% of 3-mercaptoethanol, then kept at −20° C. until analysis.

In order to ensure the lysis of the cells, the sample underwent 3 cycles of freezing-thawing and was extensively vortexed. The samples were then incubated for 5 min at 95° C. and centrifuged for 10 min at 4000 g to eliminate any insoluble residue. The proteins (10 μl of homogenate corresponding to 125 000 lymphocytes) were separated by SDS-PAGE on acrylamide gels of 10% (% T=10,% C=2.6) containing 4 M urea at constant voltage (120V). The proteins so separated were transferred semi-dry for 40 min at 13 V in the presence of tris-glycine buffer with 10% methanol, on a PVDF membrane activated beforehand with methanol.

The detection of the β2m was carried out by incubation at ambient temperature for 1 hour with a primary anti-β2m antibody diluted to 1/600 (DakoCytomation, Denmark) then again 1 hour with a secondary anti-rabbit antibody coupled to alkaline phosphatase and diluted to 1/20 000 (Sigma-Aldrich, USA). The quantification of the intensity of the bands obtained was performed with the ImageJ software application (NIH, USA).

FIG. 10A shows a photograph of the gel obtained. In the presence of glutaraldehyde, a band at 55 kDa is visible in addition to the usual band at 12 kDa. This band at 55 kDa corresponds to the HLA-β2m complex, the molecular weight corresponding to the addition of the molecular weights of a β2m molecule and of a heavy chain: 12+43 kDa=55 kDa. On the same lane, the band at 12 kDa corresponds to the free non-complexed β2m. After quantifying the intensity of each band, it was checked that the cumulative intensity of these two bands at 12 and 55 kDa corresponds to the intensity of the band at 12 kDa in the lane "without glutaraldehyde" and which corresponds to the total β2m. In both lanes, with and without glutaraldehyde, the same quantity of total proteins corresponding to the same number of lymphocytes was deposited.

In order to provide evidence that the quantification of the band at 55 kDa does indeed give the quantity of HLA-β2m complex present on the lymphocyte surface, a technique was used in parallel to purify plasma membranes from lymphocytes. This technique specifically allowed us to study proteins of the lymphocyte plasma membrane. The presence of membrane 3.2m was determined and quantified (see FIG. 10B). The result obtained is comparable to the quantification of the band at 55 kDa, which confirms that this band does indeed correspond to the membrane HLA-β2m complex. Furthermore, the proportion of membrane 3.2m relative to the total 3.2m (FIG. 10B) is equal to the ratio of intensities of the 55 kDa band/total 3.2m 12 kDa band (FIG. 10A).

The glutaraldehyde technique thus validated, was used to view and quantify the degree of incorporation on the lymphocytes isolated from human blood, of the β2m conveyed by liposomes.

Two donors, one healthy, used as a control, and the other suffering from multiple sclerosis, were selected. The second donor was chosen on account of his deficit in membrane 3.2m relative to the heavy chains of HLA-I. This patient has a membrane HC/β2m ratio equal to 1.7 which means that the lymphocyte membrane contains 69% more heavy chains than β2m.

The lymphocytes from the two donors (25 ml blood) were separated in two batches of 4 ml each; 2 ml of liposomes containing 3.2m at a concentration of 40 mg for 150 ml (Batch 40), were added to the 4 ml of lymphocytes. The $T_0$ lymphocytes were immediately collected and washed with PBS. The lymphocytes sampled at $T_{90}$, were incubated with the liposomes for 90 min. at 37° C. before being collected and washed with PBS in order to eliminate the excess liposomes not having reacted.

In each of the two conditions, we analyzed two populations of lymphocytes that had or had not been treated with glutaraldehyde (see protocol above)

The total proteins, in each condition, were separated by SDS-PAGE, then revealed by western blot. The results obtained are illustrated in FIG. 10C and we found that after quantification, contrary to the control, and in presence of glutaraldehyde, the intensity of the 55 kDa band (representing the HLA-β2m complex) had increased by 55% at $T_{90}$ relative to $T_0$.

This increase is consistent with the deficit in β2m in that patient, which cause the presence of free HLA-1 chains on the lymphocyte surface. Thus the heavy chains do indeed associate with the exogenous β2m provided by the liposomes.

The experimental approach implemented enabled the proof to be provided for the therapeutic concept of the invention, i.e. that:

It is possible to reestablish the HLA-β2m balance by an addition to the lymphocyte surface of exogenous β2m in the form of liposomes.

A patient having a deficit of β2m may incorporate more β2m than a control who has no need for it.

The incorporated β2m does indeed associate with the free HLA molecules to form HLA-β2m dimers.

In summary, the experimental data obtained confirm that it is possible, using liposome preparations of β2m, to target lymphocytes presenting free heavy chains (HC/β2m>1) for the purpose of reestablishing a HC/β2m ratio close to the physiological norm, i.e. approaching 1.

3 Toxicity Analysis of Liposome Compositions of β2m

The β2m in liposome form was tested "in vitro" for its possible toxicity on cultures of liver, kidney, skeletal muscle and heart cells of human origin.

3.1—Types of Cells Tested

The cells tested and the culture media were purchased from Sciencell Research Laboratories (6076 Corte Del Cedro, Carlsbad, Calif.).

a. HCF: Primary human cardiac fibroblast cells, batch No. 2136 Culture medium: FM (Fibroblast Medium), batch No. 5673+Fibroblast Growth Solution, batch No. 5863+FBS 10%+penicillin solution (100 U/ml)-Streptomycin (100 μg/ml), batch No. 5917 b. HREpiC: primary human renal epithelial cells, batch No. 0546 Culture medium: Epithelial Cells Medium, batch No. 5967+Epithelial Cells Growth Solution, batch No. 5855+FBS 10%+PS c. HH: primary human hepatocyte cells, batch No. 4607 Culture medium: HM (Hepatocyte Medium), batch No. 5933+Hepatocyte Growth Solution, batch No. 5722+FBS 10%+PS d. HSkMC: primary human skeletal muscle cells, batch No. 5606 Culture medium: Skeletal Muscle Cells Medium+SkMGS+FBS 10%+PS The culture flasks or dishes were placed in an incubator (Sanyo) at 37° C., 5% $CO_2$ and with saturated humidity, (bath containing ultra-pure water filtered with 0.22 μm, Nanopure, Thermo-Fisher).

The culture substrate for the primary human cells is cell culture treated plastic (TPP, Switzerland) incubated with poly-L-lysine at 2 μg/cm² (Clinisciences; Sciencell Research Laboratories, batch No. 5826, solution: 10 mg/ml) for one night in the incubator and rinsed twice with sterile ultra-pure water before inoculation.

3.2—Detachment and Dissociation of the Cell Layer

The detachment of the cell layer was carried out by eliminating the prepared medium from the culture flask then by rinsing the layer with sterile PBS (SIGMA, batch No. 088K2356) then by treating it with a solution of 0.05% trypsin (SIGMA Trypsin Ref T-1426, batch No. 020M7354), EDTA 0.2 g, NaCl 8 g, KCl 0.4 g, NaHCO3 0.58 g, Glucose 1 g (SIGMA), qs 1 liter ultra-pure water, solution sterilized by membrane filtration (PES) of 0.22µ porosity, CML batch No. 668919), the volume of the trypsin solution was adjusted to the type of flask (e.g. 1 ml for a flask of 25 cm$^2$), then the culture flask was placed at 37° C. (Sanyo incubator) for three to four minutes.

When the cells were detached from their substrate the dissociation was implemented in the presence of culture medium with serum (inhibition of the enzyme action of the trypsin) sent to and from in a pipette (from 5 to 10 ml according to the cell type).

3.3 Toxicity Test

The cells were counted using a Thoma cell (Thermo Fisher) under an optical microscope (Nikon) and were seeded in an amount of 5000 cells per well in 200 µl of their respective culture medium in a flat bottomed culture dish with 96 wells of cell culture treated plastic (NUNC, batch No. 114754) then after preparation the dishes were placed in an incubator for 24 h. The various dilutions of the substances to test were concentrated three times in 100 µl of medium without antibiotics which were added to the 200 µl of each well to treat (total volume: 300 µl). At 24 h, at 48 h and 72 h, the treated wells and the control wells were examined in accordance with the protocols for the MTT (Thiazolyl Blue Tetrazolium Bromide) [Liu Y. et al. (1997) Mechanism of cellular MTT reduction. *J. Neurochem.* 69: 581-593] and for the dosage of the proteins (Ref 23227, BCA protein Assay kit; Pierce) to evaluate the cell toxicity:

Addition of MTT solution for final concentration 25 µg/mL
Incubation 1 h at 37° C.
Aspiration of the medium
Addition of 100 µL DMSO (200 µL if saturation DO)
Reading of the dish (Biorad) at 490 nm
Computer processing with Excel.
Subtraction of the background noise using empty wells (blanks)
Determine the ratio of DO X wells/DO control wells
Trace the curve of that ratio against the drug concentration The toxicity was measured at 24 h and 48 h of treatment i.e. $t_0$+48 h and $t_0$+72 h FIGS. 11 and 12 clearly show that, even at a high dose (Batch 132), the liposome-coated β2m does not affect the viability of the hepatocytes and kidney cells, which are however sensitive to β2m. The same applies for the cells of cardiac origin and skeletal muscle cells (results not shown).

The invention claimed is:

1. A method of restoring a normal heavy chain (HC)/β2-microglobulin (β2m) molar ratio within the membrane in the membrane major histocompatibility complexes (MHC-I), comprising administering to a subject having a deficit of membrane β2m bound to HC in MHC-I present at the surface of cells of the subject, wherein the HC/β2m ratio is greater than 1, an effective amount of β2 microglobulin.

2. The method of claim 1, wherein the subject having a deficit of membrane β2-microglobulin has a HC/β2m ratio greater than 1.2.

3. The method of claim 1, wherein the subject having a deficit of membrane β2-microglobulin has a HC/β2m ratio greater than 2.

4. The method of claim 1, wherein the subject having a deficit of membrane β2-microglobulin suffers from an auto-immune disease.

5. The method of claim 2, wherein the subject having a deficit of membrane β2-microglobulin suffers from an auto-immune disease.

6. The method of claim 3, wherein the subject having a deficit of membrane β2-microglobulin suffers from an auto-immune disease.

7. The method of claim 1, wherein the subject having a deficit of membrane β2-microglobulin suffers from an auto-immune disease which is selected from the group consisting of rheumatoid polyarthritis, systemic lupus erythematosus, Sjögren's syndrome, scleroderma, fibromyalgia, myositis, ankylosing spondylitis, insulin dependent diabetes of type I, Hashimoto's thyroiditis, Addison's disease, Crohn's disease, celiac disease, multiple sclerosis and amyotrophic lateral sclerosis.

8. The method of claim 2, wherein the subject having a deficit of membrane β2-microglobulin suffers from an auto-immune disease which is selected from the group consisting of rheumatoid polyarthritis, systemic lupus erythematosus, Sjögren's syndrome, scleroderma, fibromyalgia, myositis, ankylosing spondylitis, insulin dependent diabetes of type I, Hashimoto's thyroiditis, Addison's disease, Crohn's disease, celiac disease, multiple sclerosis and amyotrophic lateral sclerosis.

9. The method of claim 3, wherein the subject having a deficit of membrane β2-microglobulin suffers from an auto-immune disease which is selected from the group consisting of rheumatoid polyarthritis, systemic lupus erythematosus, Sjögren's syndrome, scleroderma, fibromyalgia, myositis, ankylosing spondylitis, insulin dependent diabetes of type I, Hashimoto's thyroiditis, Addison's disease, Crohn's disease, celiac disease, multiple sclerosis and amyotrophic lateral sclerosis.

10. The method according to claim 1, wherein the β2-microglobulin is human β2-microglobulin.

11. The method according to claim 2, wherein the β2-microglobulin is human β2-microglobulin.

12. The method according to claim 3, wherein the β2-microglobulin is human β2-microglobulin.

13. The method of claim 1, wherein the β2-microglobulin is human β2-microglobulin which is purified, recombinant, or obtained by chemical synthesis.

14. The method of claim 1, wherein the β2-microglobulin is human β2-microglobulin which is purified, recombinant, or obtained by chemical synthesis.

15. The method of claim 3, wherein the β2-microglobulin is human β2-microglobulin which is purified, recombinant, or obtained by chemical synthesis.

* * * * *